United States Patent
Stefanchik et al.

(10) Patent No.: US 8,388,520 B2
(45) Date of Patent: Mar. 5, 2013

(54) SHAPE CONTROL ENDOSCOPE

(75) Inventors: David Stefanchik, Morrow, OH (US);
James T. Spivey, Cincinnati, OH (US);
Michael J. Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 688 days.

(21) Appl. No.: 12/392,472

(22) Filed: Feb. 25, 2009

(65) Prior Publication Data
US 2010/0217083 A1   Aug. 26, 2010

(51) Int. Cl.
*A61B 1/00*   (2006.01)
(52) U.S. Cl. .................. 600/144; 600/141; 600/148
(58) Field of Classification Search .......... 600/114–116, 600/139, 141, 142, 144, 146, 125
See application file for complete search history.

(56) References Cited

U.S. PATENT DOCUMENTS

| | | | |
|---|---|---|---|
| 4,723,864 A | 2/1988 | Umeda | |
| 4,947,827 A | 8/1990 | Opie et al. | |
| 5,005,558 A | 4/1991 | Aomori | |
| 5,105,819 A | 4/1992 | Wollschlager et al. | |
| 5,191,890 A | 3/1993 | Hileman | |
| 5,681,263 A | 10/1997 | Flesch | |
| 5,759,151 A * | 6/1998 | Sturges | 600/139 |
| 5,857,964 A | 1/1999 | Konstorum et al. | |
| 6,705,989 B2 | 3/2004 | Cuschieri et al. | |
| 6,837,847 B2 | 1/2005 | Ewers et al. | |
| 7,250,027 B2 | 7/2007 | Barry | |
| 2004/0186350 A1 * | 9/2004 | Brenneman et al. | 600/146 |
| 2005/0137456 A1 * | 6/2005 | Saadat et al. | 600/114 |
| 2005/0165415 A1 | 7/2005 | Wales | |
| 2006/0178560 A1 * | 8/2006 | Saadat et al. | 600/114 |
| 2007/0043261 A1 * | 2/2007 | Watanabe et al. | 600/144 |
| 2007/0135803 A1 | 6/2007 | Belson | |
| 2008/0132758 A1 | 6/2008 | Stefanchik et al. | |
| 2008/0183035 A1 | 7/2008 | Vakharia et al. | |
| 2008/0200762 A1 | 8/2008 | Stokes et al. | |
| 2010/0069715 A1 * | 3/2010 | Perry | 600/114 |

OTHER PUBLICATIONS

International Search Report and Written Opinion for Application No. PCT/US2010/024731, dated Sep. 13, 2010 (19 pages).
U.S. Appl. No. 11/971,410, filed Jan. 9, 2008.
U.S. Appl. No. 11/952,475, filed Dec. 7, 2007.

* cited by examiner

*Primary Examiner* — Matthew J Kasztejna
*Assistant Examiner* — Kevin G Barry, III
(74) *Attorney, Agent, or Firm* — Nutter McClennen & Fish LLP

(57) ABSTRACT

Methods and devices are provided for controlling an endoscope in a body cavity. In one exemplary embodiment, a stiffening element for an endoscopic surgical system includes an elongate member having a diameter configured for insertion and use in a channel of an endoscope. The elongate member can be movable between an unlocked position in which the elongate member is freely movable to assume a desired configuration, and a locked position in which the elongate member is maintained in a desired configuration. In one embodiment, the elongate member is formed from a plurality of links that are pivotally coupled to one another. Methods for controlling a surgical device in a body cavity, as well as systems for use in endoscopic surgeries, are also provided herein.

20 Claims, 17 Drawing Sheets

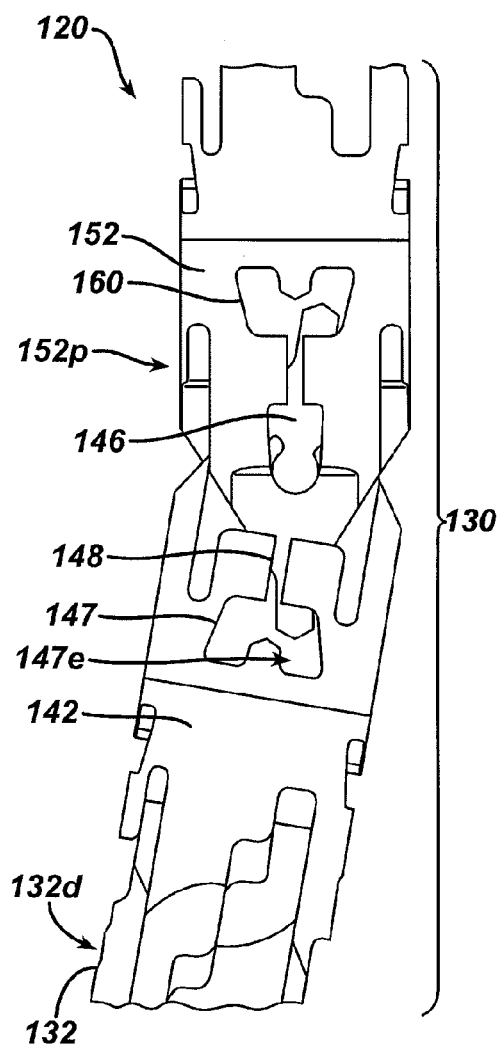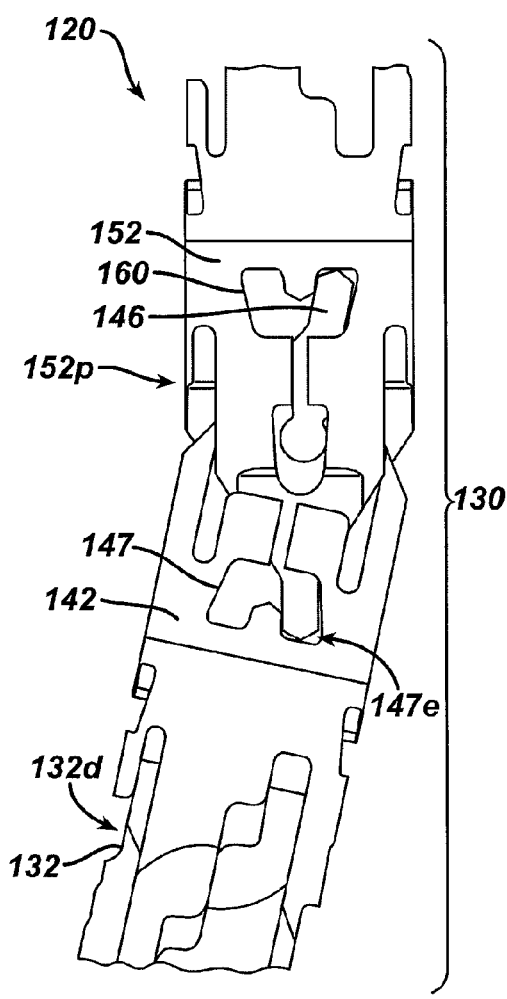
FIG. 13A
FIG. 13B

SHAPE CONTROL ENDOSCOPE

FIELD

The present disclosure relates to devices, systems, and methods for controlling an endoscope in a body cavity.

BACKGROUND

Minimally invasive surgical techniques such as endoscopies and laparoscopies are often preferred over traditional open surgeries because the recovery time, pain, and surgery-related complications are typically less with minimally invasive surgical techniques. Rather than cut open large portions of the body in order to access inner cavities, such as the peritoneal cavity, surgeons either rely on natural orifices of the body or create one or more small orifices in which surgical instruments can be inserted to allow surgeons to visualize and operate at the surgical site. Surgeons can then perform a variety of diagnostic procedures, such as visual inspection or removal of a tissue sample for biopsy, or treatment procedures, such as removal of a polyp or tumor or restructuring tissue.

Because of the rise in popularity of minimally invasive surgeries, there has been significant development with respect to the instruments used in such procedures. These instruments need to be suitable for precise placement of a working end at a desired surgical site to allow the surgeon to see the site and perform the necessary actions at such site. Often times the instruments either themselves contain a device that allows the surgeon to see the site, or else the instruments are used in conjunction with an instrument that can provide visual assistance. At least one of these types of devices, an endoscope, is typically configured with both a lens to visualize the surgical site and one or more channels through which instruments can be delivered to the surgical site for subsequent use. The instruments themselves can be used to engage and or treat tissue and other portions within the body in a number of different ways to achieve a diagnostic or therapeutic effect.

Like most surgical procedures, minimally invasive procedures require stability and precision at the surgical site. In small body cavities, strength and stability can be provided by the walls of the body cavities. In larger body cavities, however, there is generally a significant amount of three-dimensional space, and thus the walls of the larger body cavities are generally unable to provide the desired strength and stability. Walls of various organs and parts in the body are also used to assist in directing the endoscope to a desired location, for example by deflecting the endoscope against the walls in the body. In larger body cavities, however, there are no such walls to provide the desired deflection, and thus it can be difficult to deliver an endoscope to and/or through a larger body cavity. It can likewise be difficult to extend and retract the endoscope in places with a large amount of three-dimensional space. To the extent that devices, systems, and methods have been designed to help address this problem, they are limited for a number of reasons. Many still do not provide the desired strength, stability, control, and endoscope-growth capabilities. Further, devices, systems, and methods capable of providing strength, stability, or control are typically disposed on an outside of an endoscope. Disposing such devices on an outside of an endoscope adds additional instrumentation and size to be disposed in the body, which is generally not desirable, and thus increases the potential for harming the patient. It is generally preferred to minimize the number of instruments and the size of those instruments in a body, particularly during a minimally invasive procedure.

Accordingly, there is a need for new devices, systems, and procedures for controlled movement and stability within large body cavities. There is also a need for devices, systems, and methods that easily allow an endoscope to be extended and retracted within a body cavity so as to grow and reduce the size and shape of the endoscope as desired.

SUMMARY

Methods, systems, and devices are generally provided for controlling an endoscope in a body cavity, particularly one with a diameter substantially greater than the endoscope. The devices, systems, and methods described herein can be used in conjunction with an endoscopic system to assist in controlling and determining position, placement, and orientation of the endoscope. For example, stiffening elements described herein can be used to maintain at least a portion of an endoscope, e.g., a distal portion, in a desired configuration. The stiffening element(s) can be used in association with an endoscope, such as by placing the stiffening element(s) in or along side the endoscope.

In one exemplary embodiment, a stiffening element for an endoscopic surgical system includes an elongate member having a diameter that is configured for insertion and use in a channel of an endoscope. The elongate member can be movable between an unlocked position, in which the elongate member is freely movable to assume a desired configuration, and a locked position, in which the elongate member is maintained in a desired configuration. In one embodiment, the elongate member includes a plurality of links that are pivotally coupled to one another. The links can be configured such that in the unlocked position the links are freely pivotal relative to one another and in the locked position the links are prevented from pivoting relative to one another. Each link of the plurality of links can include a proximal end having opposed arms and a distal end also having opposed arms. The opposed arms of the proximal end can extend in a plane that is substantially perpendicular to a plane containing the opposed arms of the distal end. In one embodiment, the first link can be radially offset by about 90 degrees from the second link. While the diameter of the elongate member can vary, in one embodiment it is approximately in the range of two to five millimeters.

In one embodiment in which the elongate member includes a plurality of links, each link can include two elongate slots that receive the opposed arms of an adjacent link such that the arms slidably move within the elongate slots to allow pivotal movement of the links relative to one another. Such an embodiment can also include at least one locking element disposed within each link. The locking element can be movable between a first position, in which the links can be in the unlocked position, and a second position, in which the links can be in the locked position. In the second position, a portion of the locking element can extend into one of the elongate slots to prevent slidable movement of the arm therein.

In another embodiment in which the elongate member includes a plurality of links, the links can be configured to compress axially relative to one another when moved from the unlocked position to the locked position. Each link can include a receiving portion for receiving an arm of an adjacent link. The receiving portion can include an abutment that abuts the arm when the links are in the locked position to prevent movement of the arm, thereby preventing pivotal movement of the links relative to one another.

The stiffening element can also include at least one locking element disposed within the elongate member. The locking element can move between an unlocked position and a locked position in which the elongate member is in the unlocked and locked positions, respectively. Movement of the locking element can occur in a direction that is perpendicular to a longitudinal axis of the elongate member. The locking element can further include a first locking element and a second locking element disposed within the elongate member. The first and second locking elements can have substantially identical configurations. In one embodiment, the first locking element can be disposed within the elongate member at a position that is radially offset from a position of the second locking element in the elongate member. In an embodiment in which the elongate member includes a plurality of links, the locking element can be disposed within at least one of the plurality of links.

In another embodiment, the stiffening element can also include an expandable member that extends through the elongate member. The expandable member can be configured to move the elongate member between the unlocked and locked positions. In an embodiment of the stiffening element that includes both a locking element disposed within the elongate member and an expandable member, the expandable member can be disposed through at least one locking element and can be effective to move the locking element between an unlocked position and a locked position. Moving the locking element between the unlocked and locked positions can move the elongate member between the unlocked and locked positions. In embodiments in which the elongate member includes a plurality of links, moving the locking element between the unlocked and locked positions can move the link in which the locking element is disposed between the unlocked and locked positions. The expandable member can include a variety of positions, including a partially expanded position and a fully expanded position. In a partially expanded position the expandable member can maintain the locking element in the unlocked position, and in a fully expanded position the expandable member can move the locking element to the locked position. The locking element can include an opening formed therein for receiving the expandable member therethrough. The opening can have an asymmetrical shape.

In another exemplary embodiment of a stiffening element for an endoscopic surgical system, the stiffening element includes an elongate member formed from a plurality of links pivotally coupled to one another. Each link can include a locking element disposed in the link that is slidably movable in a direction transverse to a longitudinal axis of the elongate member between an unlocked position and a locked position. In the unlocked position the links can be freely pivotal to allow the elongate member to assume a desired configuration, and in the locked position the links can be prevented from pivoting relative to one another to allow the elongate member to be maintained in a desired configuration. In one embodiment, the locking element can move in a direction perpendicular to a longitudinal axis of the elongate member. The locking element can further include a first locking element and a second locking element disposed within each link. The first and second locking elements can have substantially identical configurations. Further, the first locking element can be disposed within the link at a position that is radially offset from a position of the second locking element in the link. Additionally, the first link can be radially offset by about 90 degrees from the second link. The stiffening element can also include an expandable member that extends through the locking element of each link. The expandable member can be configured to move the locking elements between the unlocked and locked positions. The expandable member can include a variety of positions, including a partially expanded position and a fully expanded position. In a partially expanded position the expandable member can maintain the locking element in the unlocked position, and in a fully expanded position the expandable member can move the locking element to the locked position. The locking element can include an opening formed therein for receiving the expandable member therethrough. The opening can have an asymmetrical shape. In one embodiment, each link of the plurality of links includes opposed arms formed on both a proximal end and a distal end of the link. The opposed arms of the proximal end can be received within opposed slots formed in a distal end of an adjacent link. Likewise, the opposed arms of the distal end can be received within opposed slots formed in a proximal end of another adjacent link. The opposed arms of the proximal and distal ends can move within the opposed slots to allow pivotal movement of the links relative to one another. The locking element can include a protrusion, and when the locking element is in the locked position, the protrusion can extend into one of the elongate slots to prevent slidable movement of the arm therein. A diameter of the elongate member can vary, but in one embodiment it can be configured for insertion and use in a channel of an endoscope. By way of non-limiting example, such a diameter can be approximately in the range of two to five millimeters.

A further exemplary embodiment of a stiffening element for an endoscopic surgical system includes an elongate member formed from a plurality of links slidably and pivotally coupled to one another. Each link can include a pair of proximal arms located on a proximal end of the link and a pair of distal arms located on a distal end of the link. The proximal arms can extend into a receiving portion in the distal end of an adjacent link and the distal arms can extend into a receiving portion in the proximal end of another adjacent link. In an unlocked position of the proximal and distal arms, the arms can be freely movable within the receiving portions to allow the elongate member to assume a desired configuration. In a locked position of the proximal and distal arms, the arms can be prevented from moving within the respective receiving portions to maintain the elongate member in a desired configuration. In one embodiment, the proximal arms can extend in a plane that is substantially perpendicular to a plane containing the distal arms. In another embodiment, each link can include an abutment disposed within the receiving portion. The abutment can be configured to prevent movement of the arms within the receiving portion when the arms are in the locked position. The links can be configured to compress axially relative to one another when moved from the unlocked position to the locked position. The stiffening element can also include a cable coupled to the plurality of links. The cable can be configured to axially compress the plurality of links. A diameter of the elongate member can vary, but in one embodiment it can be configured for insertion and use in a channel of an endoscope. By way of non-limiting example, such a diameter can be approximately in the range of two to five millimeters.

Methods for controlling a surgical device in a body cavity are also provided. In one exemplary embodiment, a first stiffening element can be advanced into a channel of an endoscopic device extending into a body cavity. The first stiffening element can be enabled to assume a desired configuration that corresponds to a desired configuration of the endoscopic device. The first stiffening element can also be stiffened such that the first stiffening element can assume the desired configuration, thereby maintaining at least a portion of the endoscopic device in the desired configuration. In one embodiment, the stiffening member is formed from a plurality of links that pivot relative to one another as the stiffening element is advanced relative to the endoscopic device. In another embodiment, the stiffening element can be stiffened by expanding an actuating member extending through the stiffening element to maintain the stiffening element in a desired configuration. Expanding the actuating member can move a plurality of locking elements disposed within the stiffening element to a locked position in which the locking elements maintain the stiffening element in the desired configuration. The method can also include at least partially contracting the actuating member to unlock the stiffening element such that the stiffening element can freely move to assume a desired configuration.

A second stiffening element can also be used in conjunction with the endoscopic device and the first stiffening element. The second stiffening element can be advanced into the channel of the endoscopic device, can be enabled to assume a desired configuration that corresponds to a desired configuration of the endoscopic device, and can be stiffening such that the second stiffening element can assume a desired configuration. Stiffening the second stiffening element to assume a desired configuration can maintain at least a portion of the endoscopic device in a desired configuration. The method can also include sequentially moving the first stiffening element and the second stiffening element relative to the endoscopic device and sequentially locking the first and second stiffening elements to move the endoscopic device relative to the body cavity. For example, in one embodiment, moving and locking the first and second stiffening elements sequentially includes positioning a distal end of the first stiffening element adjacent to a distal end of the endoscopic device and stiffening the first stiffening element so that the first stiffening element assumes a desired configuration. A distal end of the endoscopic device can be advanced distally beyond the distal end of the first stiffening element and a distal end of the second stiffening element can be positioned adjacent to the distal end of the endoscopic device. The second stiffening element can be stiffening so that the second stiffening element assumes a desired configuration. The actuating member of the first stiffening element can be at least partially unstiffened so that the first stiffening element can be freely movable to assume a desired configuration, and the distal end of the endoscopic device can be advanced distally beyond the distal end of the second stiffening element. The first stiffening element can be moved to a position adjacent to the distal end of the endoscopic device and the stiffening element can be stiffened to assume another desired configuration.

In another exemplary embodiment for controlling a surgical device in a body cavity, a first stiffening element can be advanced relative to an endoscopic device extending into a body cavity. The first stiffening element can be formed from a plurality of links that pivot relative to one another as the first stiffening element is advanced relative to the endoscopic device such that the first stiffening element assumes a desired configuration that corresponds to a desired configuration of the endoscopic device. The method can further include expanding an actuating member extending through the stiffening element to lock the plurality of links in the desired configuration, which in turn can lock a portion of the endoscopic device in the desired configuration. In one embodiment, expanding the actuating member can move a plurality of locking elements disposed within the links to a locked position in which the locking element prevents pivotal movement of the links relative to one another. The actuating member can also be at least partially contracted to unlock the plurality of links such that the plurality of links are freely pivotal relative to one another.

A second stiffening element can also be used in conjunction with the endoscopic device and the first stiffening element. The second stiffening element can be formed from a plurality of links that pivot relative to one another as the second stiffening element is advanced relative to the endoscopic device. The second stiffening element can be advanced relative to the endoscopic device such that the second stiffening element assumes a desired configuration that corresponds to a desired configuration of the endoscopic device. The method can also include sequentially moving the first stiffening element and the second stiffening element relative to the endoscopic device and locking the first stiffening element and the second stiffening element to move the endoscopic device relative to the body cavity. For example, in one embodiment, moving and locking the first and second stiffening elements sequentially includes positioning a distal end of the first stiffening element adjacent to a distal end of the endoscopic device and expanding the actuating member of the first stiffening element to lock the plurality of links of the first stiffening element. A distal end of the endoscopic device can be advanced distally beyond the distal end of the first stiffening element and a distal end of the second stiffening element can be positioned adjacent to the distal end of the endoscopic device. The actuating member of the second stiffening element can be expanded to lock the plurality of links of the second stiffening element. The actuating member of the first stiffening element can be at least partially contracted such that the plurality of links of the first stiffening element are freely pivotable relative to one another, and the distal end of the endoscopic device can be advanced distally beyond the distal end of the second stiffening element. The first stiffening element can be moved to a position adjacent to the distal end of the endoscopic device and the actuating member of the first stiffening element can be expanded to lock the plurality of links of the first stiffening element.

BRIEF DESCRIPTION OF DRAWINGS

This invention will be more fully understood from the following detailed description taken in conjunction with the accompanying drawings, in which:

FIG. 13A is a side view of another exemplary embodiment of a stiffening element for an endoscopic surgical device in an unlocked position;

FIG. 13B is a side view of the stiffening element of FIG. 13A in a locked position;

DETAILED DESCRIPTION

Figure 1A:
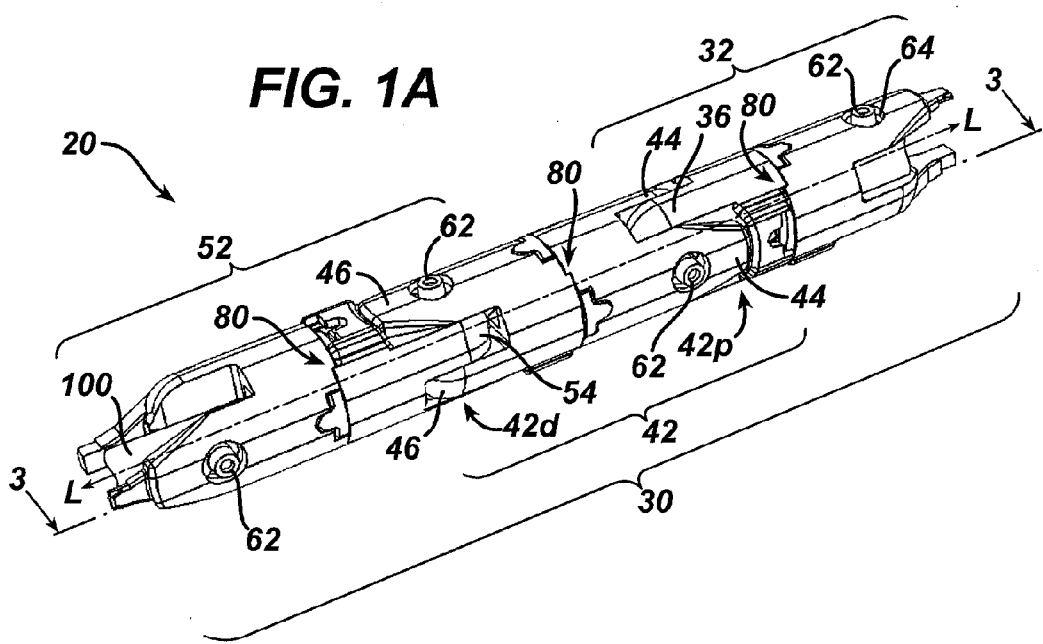
FIG. 1A is perspective view of one exemplary embodiment of a stiffening element for an endoscopic surgical system in an unlocked position.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Although the devices, systems, and methods discussed herein are generally referred to with respect to an endoscopic procedure, the devices, systems, and methods can also be used in other types of procedures, such as laparoscopic and open procedures for example. Likewise, although the present application generally refers to use of the stiffening element with an endoscope, a person skilled in the art will appreciate that the stiffening element can be used to stiffen any device that is inserted into the body, for example, tissue graspers. Reference to proximal and distal ends are for convenience only, and can be interchanged in practice. With respect to the present application, generally a distal end refers to a portion of a component that is closer to the tip of the described component, and thus, with respect to an endoscope, is generally a portion of a component that is disposed in the body before the component's respective proximal end is disposed in the body.

A stiffening element is generally provided for use in an endoscopic surgical system. The stiffening element can be an elongate member disposed within an endoscope, for example in a working channel of an endoscope, or along side the endoscope. The elongate member of the stiffening element can be movable between an unlocked position in which the elongate member is freely movable to assume a desired configuration, and a locked position in which the elongate member is maintained in a desired configuration. In some embodiments, the elongate member can include a plurality of links. The plurality of links can be configured in a manner such that in the unlocked position the links are freely pivotal relative to one another, and in the locked position the links are prevented from pivoting relative to one another.

The endoscope can also include additional mating features, for example a rail or a channel, and the stiffening element can be disposed along or within such mating features. By way of non-limiting examples, the endoscopes and related mating features discussed in U.S. Patent Application Publication No. 2008/0132758 of Stefanchik et al., filed on Dec. 5, 2006, and entitled "Independent Articulating Accessory Channel," U.S. Patent Application Publication No. 2008/0183035 of Vakharia et al., filed on Jan. 26, 2007, and entitled "Endoscopic Accessory Control Mechanism," and in U.S. patent application Ser. No. 11/971,410 of Stefanchik et al., filed on Jan. 9, 2008, and entitled "Articulating Surgical Device and Method of Use," each of which is hereby incorporated by reference in its entirety, are types of endoscopic surgical systems in which the stiffening element can be incorporated by disposing it within the endoscope, along side the endoscope, or along or within respective mating features. The stiffening element can be capable of transmitting a force to the endoscope to maintain a desired position, and further, it can be capable of controlling a location of the endoscope to assist in directing it to a desired location.

In embodiments in which the stiffening element includes links, the links can have a variety of configurations. Generally, the links can be configured to slide and/or pivot with respect to each other. In one exemplary embodiment, each link includes a proximal end with opposed arms and a distal end with opposed arms. The opposed arms of the proximal end can extend in a plane that is substantially perpendicular to a plane containing the opposed arms of the distal end. Further, the opposed arms of the proximal end of a link can be coupled to a receiving portion of an adjacent link such that the links are pivotal to one another. In piecing the links together, each link can be radially offset by about 90 degrees from an adjacent link. Accordingly, in one embodiment a second link can be radially offset by about 90 degrees with respect to a first link, a third link can be radially offset by about 90 degrees with respect to the second link and about 180 degrees with respect to the first link, a fourth link can be radially offset by about 90 degrees with respect to the third link, about 180 degrees with respect to the second link, and about 270 degrees with respect to the first link, and a fifth link, which is radially offset by about 90 degrees with respect to the fourth link. This configuration can lead to a sort of spiral design that eventually forms an approximately straight line as the links are pieced together. This configuration also allows the plurality of links to pivot in any direction, thereby enabling the plurality of links to achieve any desired shape. Each link can further be divided into a first and second portion, each portion having first and second ends. The second end of the first portion can be coupled to the second end of the second portion to form a link.

In one embodiment, the second portion can be radially offset by about 90 degrees with respect to the first portion to form the link. The first and second portions can optionally have one or more locking elements disposed therebetween. The locking elements can be movable between an unlocked position in which the links of the stiffening element are in the unlocked position and a locked position in which the links of the stiffening element are in the locked position. When the stiffening element is in an unlocked position, an endoscope associated with the stiffening element is free to assume any desired configuration. When the stiffening element is in a locked position, an associated endoscope assumes the configuration of the stiffening element when it is locked. Sequential locking and unlocking of one or more stiffening elements, coupled with sequential distal movement of the endoscope and the stiffening element(s), can be effected to advance the endoscope in a desired configuration or orientation.

An actuating member can be used to move the stiffening element between the unlocked and locked positions. The actuating member can be part of the stiffening element itself, or alternatively, it can be a separate component configured to unlock and lock the stiffening element. While a variety of actuating members can be used, two exemplary embodiments include a cable coupled to at least one of the plurality of links and an expandable member disposed within the plurality of links and configured to expand and contract to lock and unlock the stiffening element. The actuating member can be configured to lock any number of links at the same time. In one embodiment, it is configured to lock all of the links at the same time, thereby preventing a domino effect. In another embodiment, the actuating member is configured to lock a subset of the links. Still in other embodiments, multiple actuating members can be used to selectively lock portions of the endoscope as desired. In such embodiments, the endoscope can be used selectively in manners similar to those described in U.S. patent application Ser. No. 11/952,475 of Stefanchik et al., filed on Dec. 7, 2007, and entitled "Selective Stiffening Devices and Methods," which is hereby incorporated by reference in its entirety. Stiffening devices disclosed in U.S. patent application Ser. No. 11/952,475 can be used in combination with the teachings herein, or alternatively, the stiffening elements disclosed herein can be used in place of the stiffening devices disclosed in U.S. patent application Ser. No. 11/952,475.

The elongate member can have a variety of shapes and sizes that will depend on a number of factors, including, for example, the intended use of the elongate member. In one exemplary embodiment it can be configured for insertion and use in a channel of an endoscope. In some embodiments the diameter is approximately in the range of about 2 to 8 millimeters, or more precisely, in the range of about 2 to 5 millimeters. In embodiments in which the elongate member includes links, any number of links can be used, and any size of links can be used. The number and size of the links will also depend on a number of factors, including, for example, the surgical procedure and size and location of the body cavities involved. In one embodiment, approximately 200 links are used to form a stiffening element that has a length of approximately three feet. In embodiments in which the stiffening element is disposed in a working channel of an endoscope, it can be desirable to allow for some clearance between the stiffening element, an instrument disposed in the working channel, and the working channel itself. In one exemplary embodiment, a diameter of the links is approximately 2.4 millimeters and a diameter of a working channel of an endoscope is approximately 3.7 millimeters. It is generally desirable to have at least one millimeter of clearance between the stiffening element and the working channel when the stiffening element is disposed in the working channel. In an embodiment in which the links are configured in a spiral design such that they are approximately straight, twelve links, each having a 3.6 millimeter diameter, can lead to an approximately straight configuration.

The various embodiments of the stiffening elements, e.g., FIGS. 1A-16C, are each described with respect to a single stiffening element. It is understood that, in use, one or more stiffening elements can be associated with a single endoscope to effect desired placement, positioning, and orientation of the endoscope. In fact, methods of using the stiffening elements of the invention with an endoscope are described with reference to FIGS. 17A-17F, in the context of two stiffening elements being associated with a single endoscope.

One exemplary embodiment of a stiffening element for an endoscopic surgical system is illustrated by FIGS. 1A-12B. The stiffening element 20 (only part of which is shown) is an elongate member formed from a plurality of links 30 that are pivotally coupled to one another. While the illustrated embodiments include three links 32, 42, 52, any number of links can be used. Each link 32, 42, 52 can include a locking element 80 disposed therein. The locking element 80 can have a variety of configurations, but in one exemplary embodiment it is slidably movable in a direction that is transverse to a longitudinal axis L of the elongate member. It can move between an unlocked position, illustrated in FIGS. 1A and 12A, in which the links 32, 42, 52 are freely pivotal to allow the elongate member to assume a desired configuration, and a locked position, illustrated in FIGS. 1B and 12B, in which the links 32, 42, 52 are locked in a desired configuration. Although the illustrated embodiments show the elongate member in a generally straight configuration in both the unlocked and locked positions, in other embodiments the elongate member can be in a desired configuration in either or both of the unlocked and locked positions. The desired configuration in the unlocked and locked positions can be similar or different, depending at least, in part, on the one or more shapes desired during the course of using the device. The elongate member can move in any desired direction.

FIGS. 1A-3B show three links 32, 42, 52 of the plurality of links 30 of the stiffening element 20. As illustrated, each of the three links 32, 42, 52 is configured in a substantially identical manner, although in other embodiments, two or more configurations of links can be used to form the elongate member. It can be beneficial to use a substantially similar configuration for each link to reduce the costs and difficulties of manufacturing and repairing such devices. In some embodiments, each link can be radially offset by about 90 degrees with respect to an adjacent link. As shown, the first link 32 is radially offset by about 90 degrees with respect to the second link 42 and the second link 42 is radially offset by about 90 degrees with respect to the third link 52. While in the illustrated embodiment the first link 32 is radially offset by about 180 degrees with respect to the third link 52, in other embodiments the first and third links 32, 52 can have approximately the same orientation. The links 30 can be configured to couple to each other in a variety of ways, as will be discussed in greater detail below. In one embodiment, disposing the links 30 in a continued radially offset manner can result in a spiral design that eventually forms an approximately straight line as viewed from a distal end of the elongate member. This configuration can also cause all the plurality of links 30 to pivot in any direction, thereby enabling the plurality of links 30 to achieve any desired shape.

FIGS. 4-8 illustrate one embodiment of a single link, as shown the second link 42, of the plurality of links 30 of the elongate member. A proximal end 42p of the link 42 and a distal end 42d of the link 42 can each include a pair of opposed arms 44, 46, respectively. The opposed arms 44, 46 of the proximal and distal ends 42p, 42d can be configured to mate to adjacent links to assist in forming the plurality of links 30 of the elongate member. As illustrated, the opposed arms 44 of the proximal end 42p extend in a plane A that is substantially perpendicular to a plane B containing the opposed arms 46 of the distal end 42d. Each link can include one or more elongate slots 48, 50 formed therein for receiving opposed arms of an adjacent link, for example arms 34, 36 of link 32, in a manner that allows the arms to slidably move within the elongate slots 48, 50, thereby allowing pivotal movement of the links relative to one another. In the three link embodiment of FIGS. 1A-3B, the opposed arms 44 of the proximal end 42p of the second link 42 are substantially parallel to opposed arms 36 of a distal end 32d of the first link 32 and the opposed arms 46 of the distal end 42d of the second link 42 are substantially parallel to opposed arms 54 of a proximal end 52d of the third link 52. While in the illustrated embodiment the slots 48, 50 are located below the opposed arms 44, 46, in other embodiments the slots can be formed on or at other locations of the link 42, and further, can have a variety of shapes, sizes, and configurations. For example, in the illustrated embodiment, one of the arms of each of the opposed arms 44, 46 is thicker than a second arm of the opposed arms 44, 46, and thus the slots 48, 50 can be configured to receive arms of varying thicknesses. Generally, the slots 48, 50 can be configured to mechanically receive and maintain the coupled relationship between the link 42 and an adjacent link. Further, one or more attachment mechanisms, such as screws or pins, can be used to couple adjacent links together. In the illustrated embodiments, a link receiving portion 62 can be configured to engage a pin portion 64 (as shown at least in FIG. 2) of an adjacent link. While in the illustrated embodiment the link receiving portion 62 is located on the same side of the link 42 as the thin arm of the opposed arms 44, 46 and the pin portion 64 is located on the same side of the link 42 as the thicker arm of the opposed arms 44, 46, a variety of configurations can be used which allow the links to be pivotally coupled together. Additionally, an aperture 66 for receiving an actuating member can also be formed within the link 42.

The link 42 can further be divided into a first portion 70 and a second portion 72 with each portion 70, 72 having a first end 70a, 72a and a second end 70b, 72b, respectively. Each of the first and second portions 70, 72 can be configured in substantially the same manner, thereby easing the manufacture and repair of each portion of the link 42, and in the illustrated embodiment the first portion 70 is radially offset from the second portion 72 by about 90 degrees. The second ends 70b, 72b of each of the first and second portions 70, 72 can be coupled together to form the link 42. In the illustrated embodiment a locking element 80, and more particularly a first locking element 82 and a second locking element 84, are disposed therebetween. As shown, the first locking element 82 is disposed in the second end 70b of the first portion 70 of the link 42 and the second locking element 84 is disposed in the second end 72b of the second portion 72 of the link 42. While in the illustrated embodiment the link 42 includes the first and second portions 70, 72, in other embodiments the link 42 can be a unitary structure, can include more than two portions, or can be made of two or more portions that are not substantially similar. In the illustrated embodiment, the first and second locking elements 82, 84 are configured to move between the unlocked and locked positions cooperatively, although in other embodiments various locking elements 80 of the plurality of links 30 can be configured such that only some locking elements 80 move to an unlocked position while others maintain a locked position and/or an unengaged position.

Figure 2:
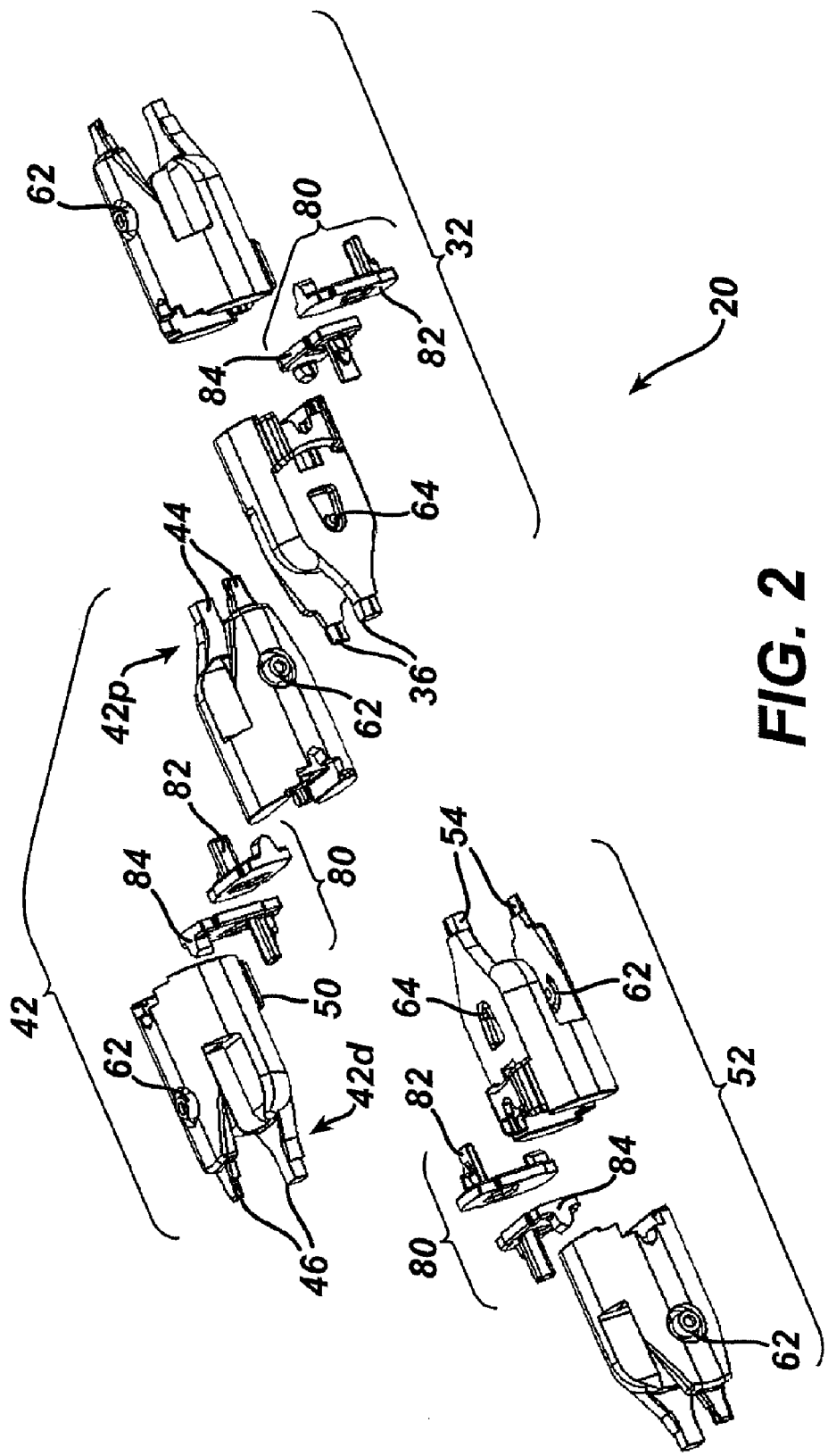
FIG. 2 is an exploded perspective view of the stiffening element of FIG. 1A with an expandable member removed.
Figure 3A:
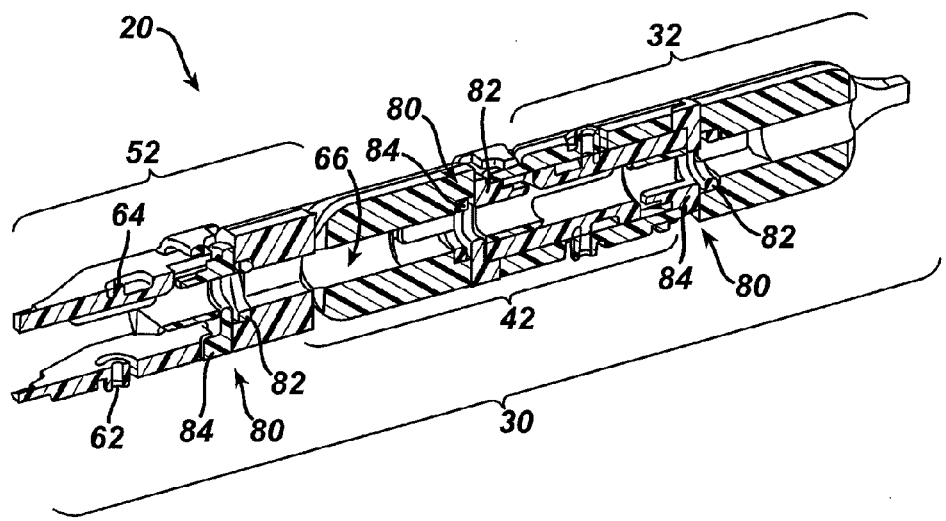
FIG. 3A is a perspective cross-section view of the stiffening element of FIG. 1A taken along line 3-3 and with an expandable member removed.
Figure 3B:
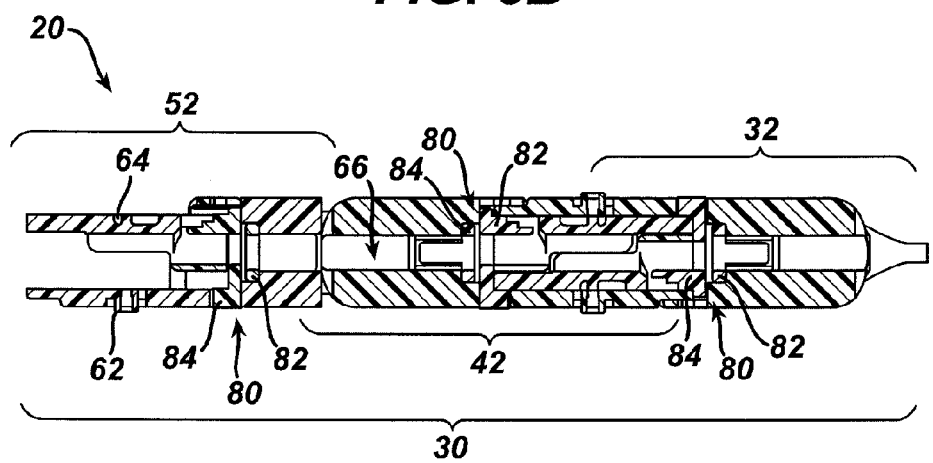
FIG. 3B is a side cross-section view of the stiffening element of FIG. 1A taken along line 3-3 and with an expandable member removed.
Figure 4:
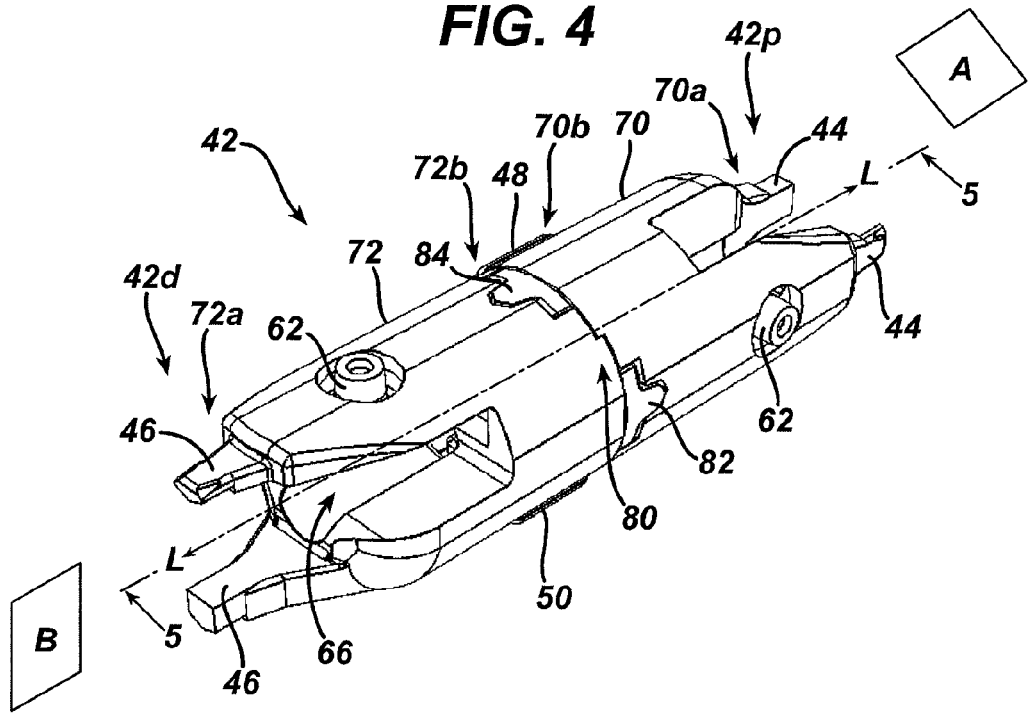
FIG. 4 is a perspective view of one link of the stiffening element of FIG. 1A.
Figure 5:
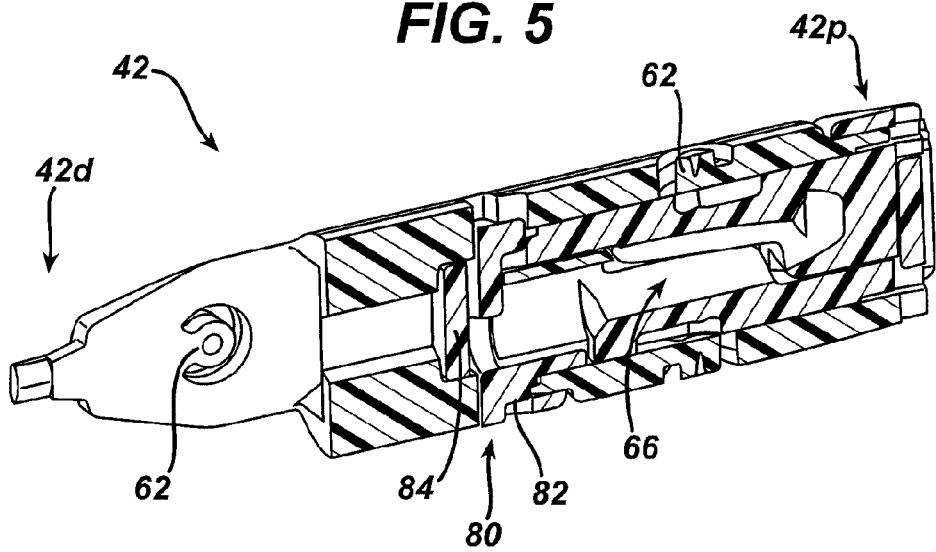
FIG. 5 is a perspective cross-section view of the link of FIG. 4 taken along line 5-5.
Figure 6:
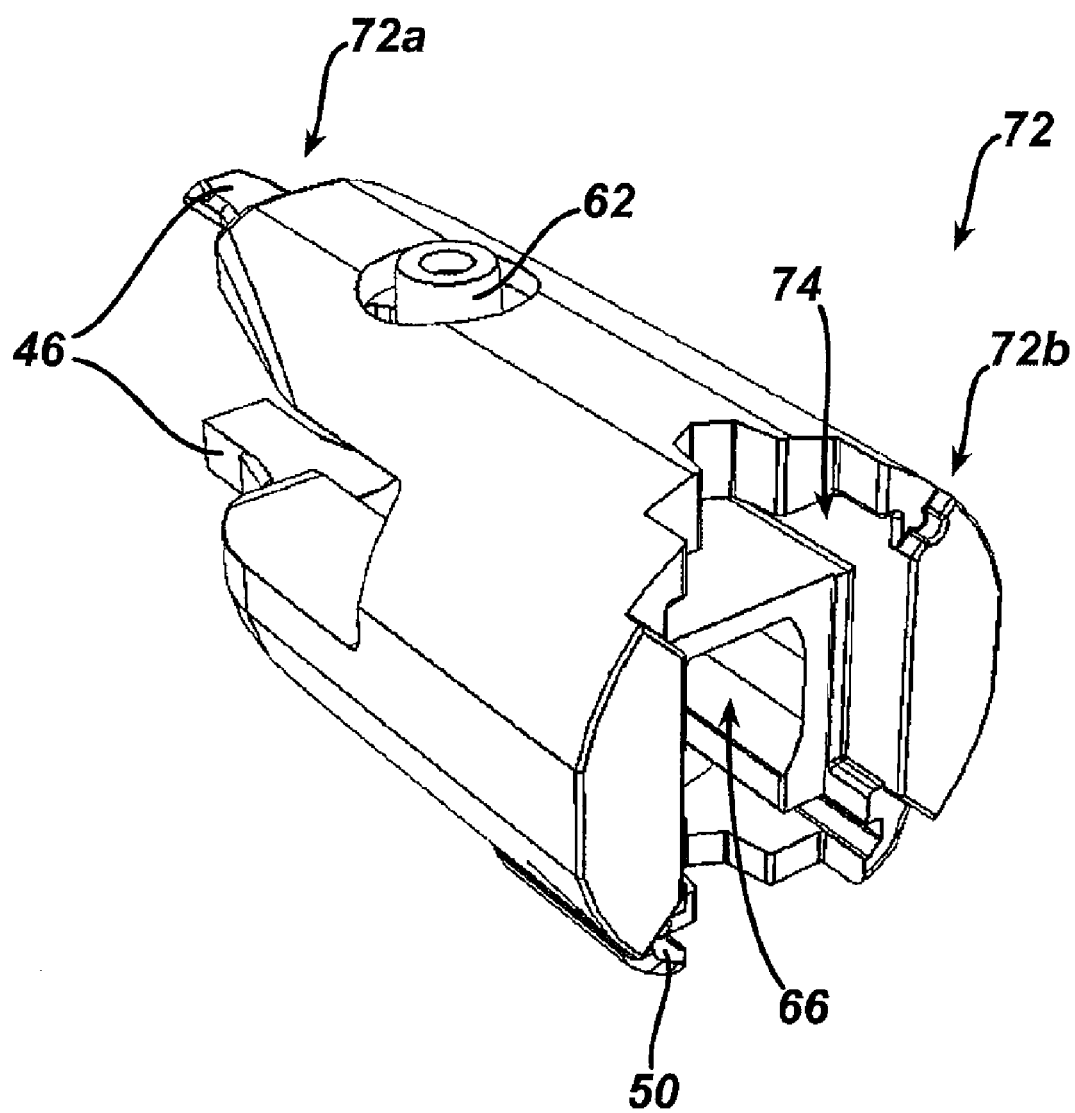
FIG. 6 is a perspective back view of a second portion of the one link of FIG. 4.
Figure 7:
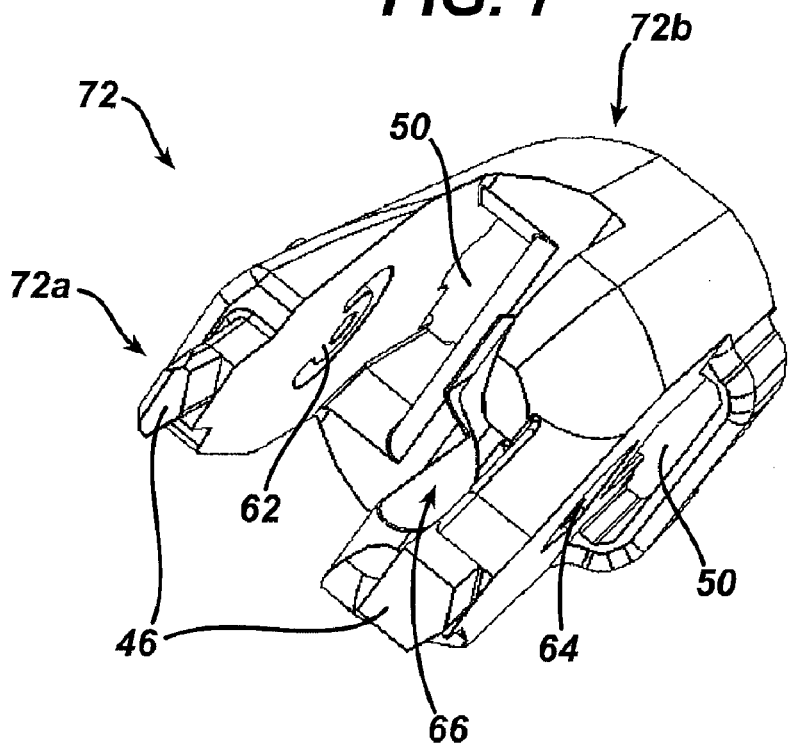
FIG. 7 is a perspective front view of the second portion of FIG. 6.
Figure 8:
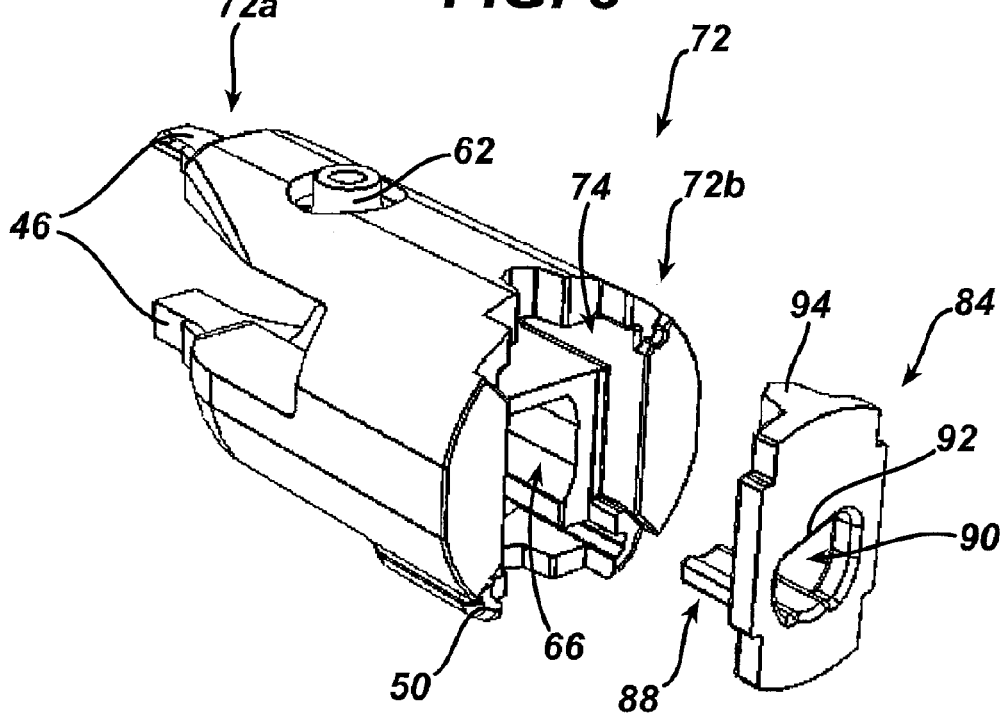
FIG. 8 is a perspective back view of a second portion and a second locking element of the one link of FIG. 4.

Each link includes one or more locking elements 80 disposed therein. The locking element 80 can slidably move in a direction transverse to the longitudinal axis L of the elongate member between an unlocked and locked position. More particularly, the locking element 80 can be movable in a direction perpendicular to the longitudinal axis L of the elongate member. In the illustrated embodiment, each link 32, 42, 52 includes the first locking element 82 and the second locking element 84 disposed therein. Each of the first and second locking elements 82, 84 can be disposed in the links 32, 42, 52 in a manner that allows the locking elements 82, 84 to be slidably movable to unlock and lock the stiffening element 20. More particularly, each of the first and second locking elements 82, 84 move in directions that are transverse to the longitudinal axis L of the elongate member. In one embodiment, the first locking element 82 is radially offset from a position of the second locking element 84. For example, the first locking element 82 can be radially offset by about 90 degrees with respect to the second locking element 84, as illustrated in FIG. 2.

Figure 9:
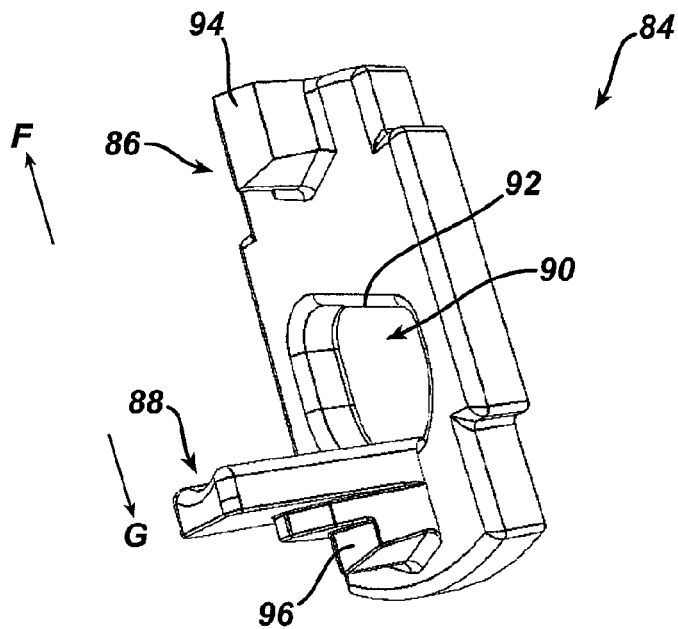
FIG. 9 is a perspective view of the second locking element of FIG. 8.
Figure 10:
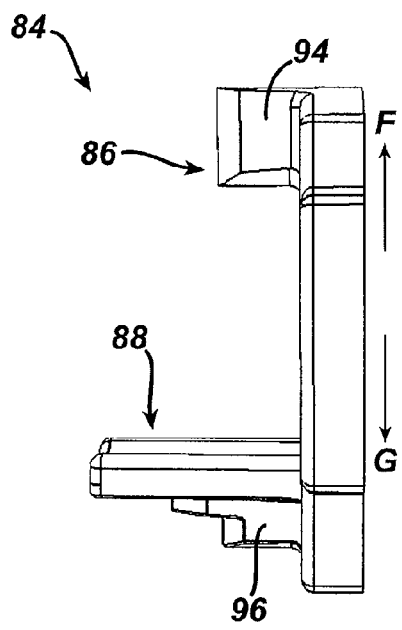
FIG. 10 is a perspective side view of the second locking element of FIG. 8.
Figure 11:
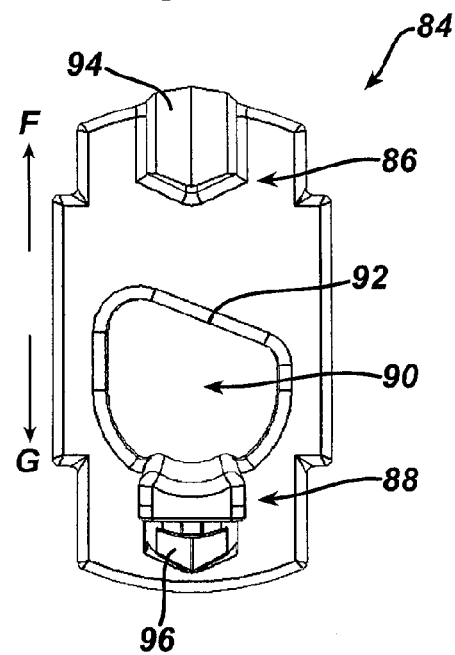
FIG. 11 is a perspective front view of the second locking element of FIG. 8.

The first and second locking elements 82, 84, like many of the other components of the stiffening element 20, can have substantially similar configurations to ease the manufacture and repair of the locking elements 82, 84. As illustrated in FIGS. 9-11, in one embodiment a locking element 84 can include two force-receiving surfaces 86, 88 with an aperture 90 disposed therebetween. Typically, one of the force-receiving surfaces has a larger surface area than the other, and as illustrated the second force-receiving surface 88 is larger than the first force-receiving surface 86. Accordingly, as a force is applied to the locking element 84, for example through the aperture 90, the force can first be received by the smaller, first force-receiving surface 86 to move the locking element 84 to a first position, in a direction F toward the first force-receiving surface 86. As a force being applied to the locking element 84 increases, the larger, second force-receiving surface 88 can receive more of the force and move the locking element 84 to a second position, in a direction G toward the second force-receiving surface 88. In the illustrated embodiment, the aperture 90 has an asymmetrical shape, which can assist in distributing the forces between the first and second force-receiving surfaces 86, 88. As shown, the asymmetrical shape includes a flat portion 92 disposed proximal to the first force-receiving surface 86. The locking element 84 can also include one or more protrusions 94, 96 which are configured to extend into one or more of the elongate slots 48, 50 to prevent slidable movement of an adjacent arm therein when the locking element 84 is in the locked position. In the illustrated embodiment, the first protrusion 94 includes the first force-receiving surface 86 and the second protrusion 96 is coupled to the second force-receiving surface 88. In other embodiments, the protrusions 94, 96 and respective force-receiving surfaces 86, 88 can be part of the same structure, integrally formed, or separately formed but coupled such that application of a certain amount of force on the force-receiving surfaces 86, 88 can move the protrusions 94, 96 into and out of the slots 48, 50 as desired.

Figure 12A:
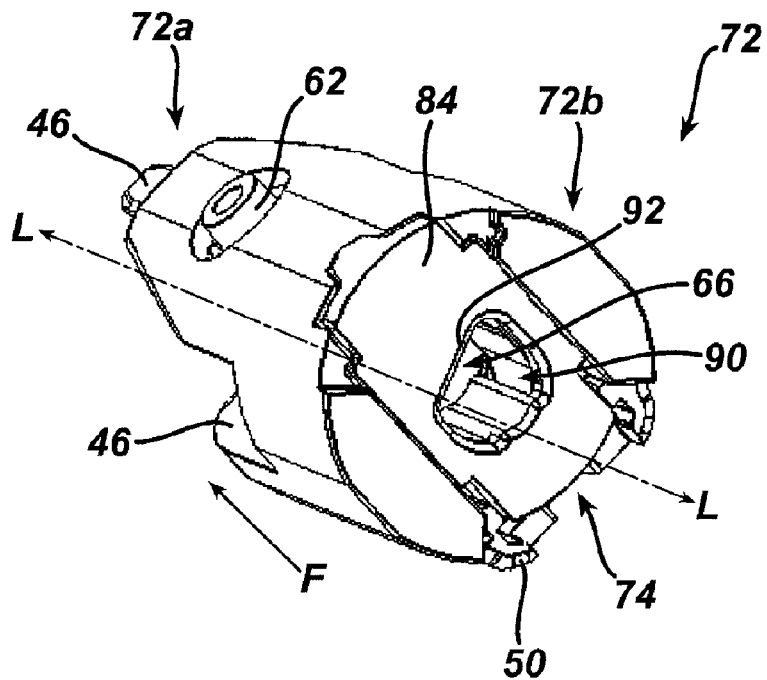
FIG. 12A is a perspective back view of the second portion of FIG. 8 with the second locking element coupled to the second portion and in an unlocked position.
Figure 12B:
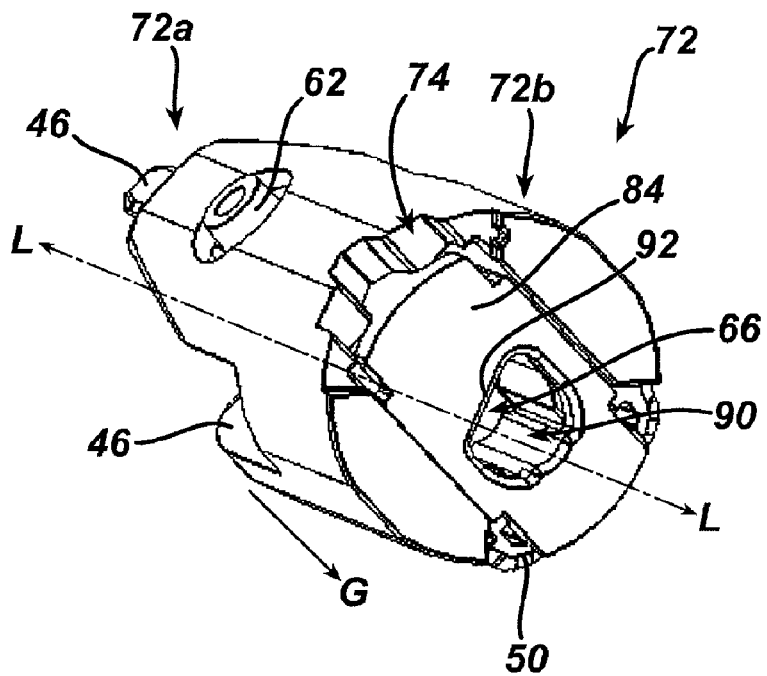
FIG. 12B is a perspective back view of the second portion of FIG. 8 with the second locking element coupled to the second portion and in a locked position.

The locking element 80 can be disposed in any portion of the link 42, but in the illustrated embodiment the second locking element 84 is disposed in the second end 72b of the second portion 72 of the link 42 and the first locking element 82 is disposed in the second end 70b of the first portion 70 of the link 42, adjacent to the second locking element 84. Each of the first and second locking elements 82, 84 can move between the unlocked and locked positions as a force is applied thereto. FIGS. 12A and 12B illustrate the unlocked and locked positions of the locking element 84, respectively. In the unlocked position, a force has been applied to the locking element 84 such that the force was large enough to push on the first force-receiving surface 86 and push the locking element 84 to the unlocked position. As a force continues to increase, eventually the force can be large enough to apply a great enough force on the second force-receiving surface 88 and push the locking element 84 to the locked position, as illustrated in FIG. 12B. Because the surface area of the second force-receiving surface 88 is larger than the surface area of the first force-receiving surface 86, as the force increases the second force-receiving surface 88 eventually has a force supplied to it that is greater than the force supplied to the first force-receiving surface 86, thereby disengaging the locking element 84 from the unlocked position and moving it to the locked position. When no force is supplied to the locking element 84, the locking element 84 can generally be loose and unengaged in neither the unlocked nor locked position.

The second end 72b of each second portion 72 of the link 42 can be configured to receive the locking element 84. As illustrated in FIGS. 12A and 12B, the second end 72b includes a cut-out portion 74 for receiving the locking element 84. The cut-out portion 74 can be configured to allow the locking element 84 to move in a direction transverse to the longitudinal axis L of the elongate member between unlocked and locked positions. Further, although in the illustrated embodiments first and second locking elements are used, in other embodiments the locking element 80 can be a single locking element, or alternatively, more than two locking elements can be used to form the locking element 80.

Figure 1B:
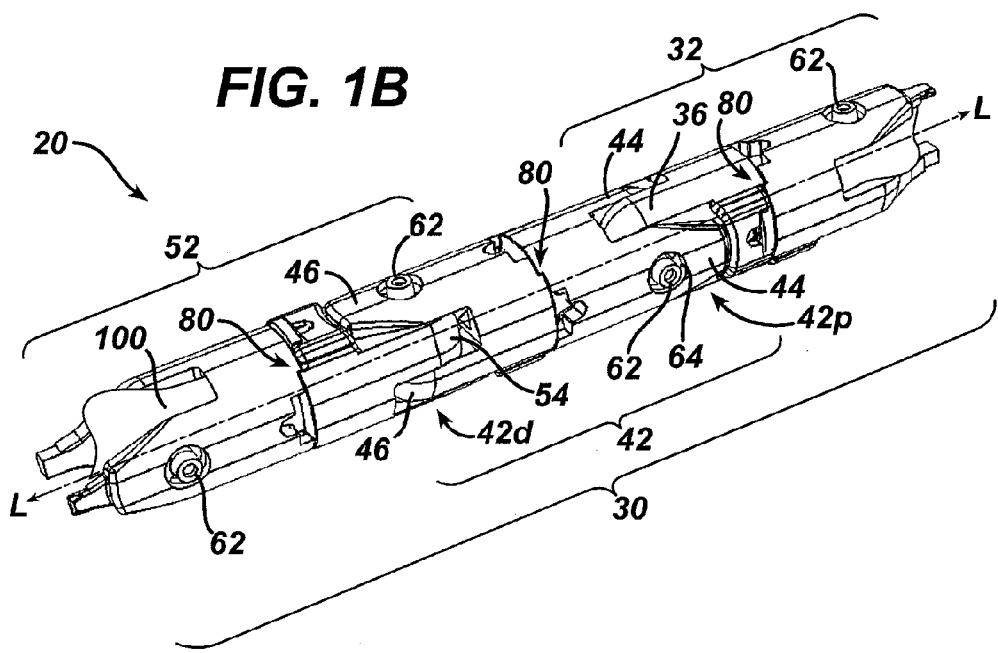
FIG. 1B is a perspective view of the stiffening element of FIG. 1A in a locked position.

The one or more forces that can be applied to the elongate member, and more particularly the locking element 80 in the illustrated embodiment, can come in a variety of forms and actuating members, but as illustrated in FIGS. 1A and 1B, the force is supplied by an expandable member 100 disposed in at least part of the elongate member. As illustrated, the expandable member 100 extends through the elongate member, passing through the apertures 90 of the locking elements 80 and apertures 66 of the links 30, which are configured for receiving the expandable member 100. The waved lines of the expandable member 100 in FIGS. 1A and 1B indicate that the expandable member 100 does not necessarily terminate at that location, but rather, can continue beyond the links or through additional links of the stiffening element 20, just as additional links can be added to the plurality of links 30 of the stiffening element 20. The expandable member 100 can be expanded and contracted to allow the locking member 80 to move between unengaged, unlocked, and locked positions. In one exemplary embodiment, the expandable member 100 is a thin bladder capable of expanding and contracting. Although the bladder can generally be thin, it is typically difficult to puncture. Materials such as silicon can be used to form the expandable member 100. Any number of devices can be used to selectively inflate and contract the expandable member 100, such as, by way of non-limiting example, a squeeze bulb. The squeeze bulb can supply a fluid to inflate the expandable member 100, and further, can remove a fluid to contract the expandable member 100.

In use, the expandable member 100 can be located within the elongate member, extending through the plurality of links 30 and locking elements 80. The expandable member 100 can begin in an uninflated, collapsed position in which the locking elements 80 disposed within the plurality of links 30 are free to slide therein without necessarily becoming engaged in either the unlocked or locked positions. As the expandable member 100 is inflated, it can expand to a partially-inflated position, which is shown in FIG. 1A. While the partially-inflated position can have many different configurations, in the illustrated embodiment the expandable member 100 is inflated until the expandable member 100 has a substantially uniform shape throughout its length. When the expandable member 100 is in the partially-inflated position, spring loading in the first direction F can occur, as shown in FIG. 12A, to move the locking element 80 to the unlocked position. In the unlocked position, the first force-receiving surfaces 86 can be held in particular locations that allow the links 30 to freely pivot to a desired configuration, for example a curved configuration. In one embodiment, the force applied to the first force-receiving surfaces 86 to place the locking elements 80 in the unlocked position is approximately one pound while a negligible amount of force, or no force at all, is applied to the second force-receiving surfaces 88 by the expandable member 100.

The expandable member 100 can be further inflated, for example by overinflating it to a fully-expanded position as shown in FIG. 1B. As the expandable member 100 continues to be expanded, the design of the apertures 90 of the locking elements 80 can be such that the second force-receiving surfaces 88 begin to receive a substantial amount of force until the amount of force received by the second force-receiving surfaces 88 is greater than the amount of force received by the first force-receiving surfaces 86. This can result in spring loading in the second direction G, as shown in FIG. 12B, to move the locking elements 80 to the locked position. In such an embodiment, further expansion of the expandable member 100 is constrained by the size of the apertures 90 of the locking elements 80, and in embodiments in which the apertures 90 are asymmetrically shaped, the asymmetric shapes can further create force distribution toward the second force-receiving surfaces 88. In one embodiment in which the locking elements 80 are disposed in the locked position, the force applied to the first force-receiving surfaces 86 is approximately 3 pounds and the force applied to the second force-receiving surfaces 88 is approximately 10 pounds. A person skilled in the art would recognize that these force values can be easily adapted for desired uses, and thus the devices, systems, and methods discussed herein are in no way limited by the recited forces used to move the locking elements 80 between the unengaged, unlocked, and locked positions.

Although the expandable member is generally discussed as passing through a length of the elongate member, in other embodiments the expandable member can be disposed in only a portion of an elongate member such that only a portion of the elongate member is configured to be unlocked and locked. In other embodiments, a plurality of expandable members can be disposed in the elongate member and each can be configured to selectively unlock and lock portions of an elongate member as desired. Allowing selective unlocking and locking of the elongate member can allow for portions of an instrument to be maintained in a rigid location while other portions are free to pivot and move. Such selective stiffening can be desirable for operating certain types of instruments within a body cavity.

While any size and shape of the plurality of links 30, as well as the various components of each link 32, 42, 52 and the stiffening element 20 as a whole, can be used, and decisions related to the size and shape will depend on a number of factors, including, for example, the intended use of the stiffening element 20, in one embodiment a length of a single link is approximately 4.86 millimeters and a diameter is approximately 2.5 millimeters. Likewise, a variety of materials can be used to form the links 30 depending on a number of factors, such as the intended use of the stiffening element 20. The links 30 can be formed from one or more materials, but in one embodiment they are formed from a single material and the single material is stainless steel. In another embodiment a shape-memory alloy, such as a nickel-titanium alloy, can be used. Further, one or more of the links 30 can optionally be disposed in a sheath. The sheath can serve a number of purposes, such as to protect the links from foreign materials becoming disposed therein, and in some embodiments a sheath can be disposed around the entirety of the length of the links 30.

Figure 14:
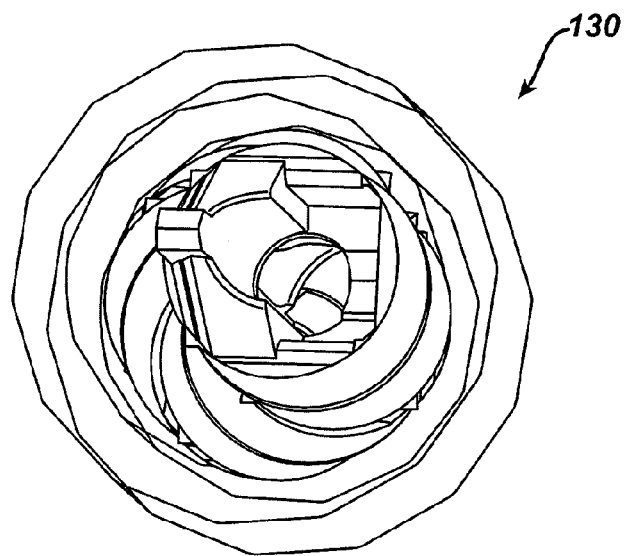
FIG. 14 is an end view of the stiffening element of FIG. 13A.
Figure 15:
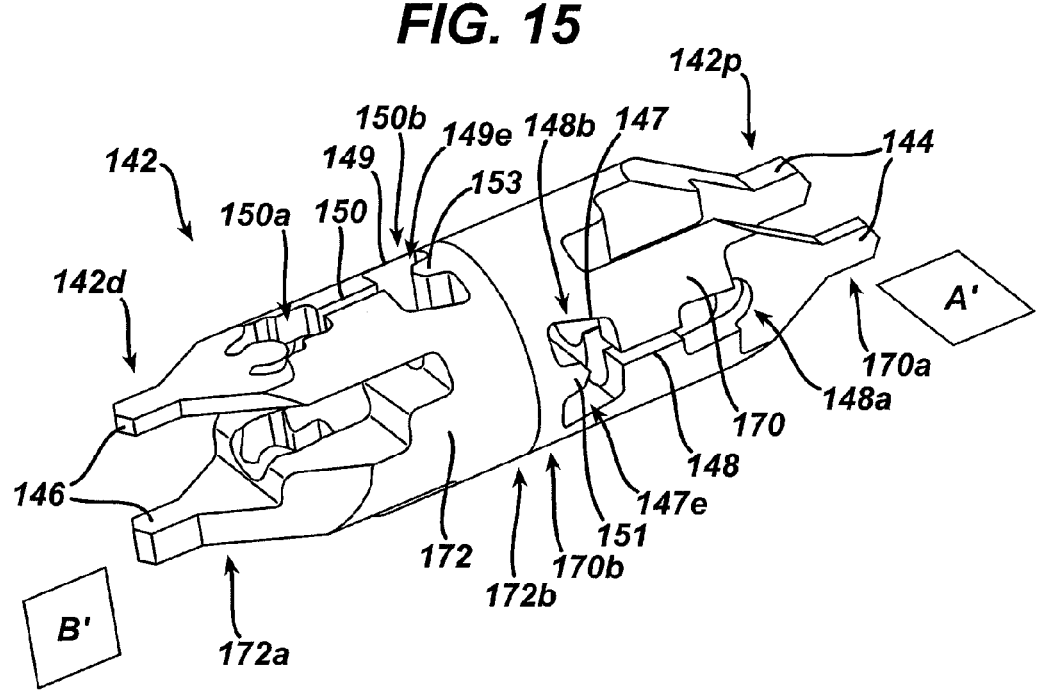
FIG. 15 is a perspective view of one link of the stiffening element of FIG. 13A.

Another exemplary embodiment of a stiffening element 120 for an endoscopic surgical system is illustrated by FIGS. 13A-15. The stiffening element is an elongate member formed from a plurality of links 130 that are slidably and pivotally coupled to one another to move between unlocked and locked positions. Each link, such as link 142 as best illustrated in FIG. 15, can include a pair of proximal arms 144 located on a proximal end 142p thereof and a pair of distal arms 146 located on a distal end 142d thereof. The proximal arms 144 can extend into a receiving portion (not shown) of a distal end 132d of an adjacent link 132 and the distal arms 146 can extend into a receiving portion 160 in a proximal end 152p of another adjacent link 152. One way in which the stiffening element 120 can move between the unlocked and locked positions can be to move the proximal and distal arms of the links 130 between unlocked and locked positions. For example, in an unlocked position the arms can be freely movable within adjacent receiving portions to allow the elongate member to assume a desired configuration, such as a curved configuration, and in a locked position the arms can be prevented from moving within adjacent receiving portions to maintain the elongate member in a desired configuration. In one embodiment the links 130 can be configured to compress axially to move the arms between the unlocked and locked configurations. Similar to other embodiments of a stiffening element disclosed herein, a desired configuration in the unlocked and locked positions can be similar or different, depending at least, in part, on the one or more shapes desired during the course of using the device.

FIGS. 13A and 13B show a portion of three links 132, 142, 152 of the plurality of links 130 of the stiffening element 120. As illustrated, each of the three links 132, 142, 152 is configured in a substantially identical manner, although in other embodiments, two or more configurations of links can be used to form the elongate member. It can be beneficial to use a substantially similar configuration for each link to reduce the costs and difficulties of manufacturing and repairing such devices. As shown, each link is radially offset by about 90 degrees with respect to an adjacent link. More specifically, in the illustrated embodiment the first link 132 is radially offset by about 90 degrees with respect to the second link 142 and the second link 142 is radially offset by about 90 degrees with respect to the third link 152. While in the illustrated embodiment the first link 132 is radially offset by about 180 degrees with respect to the third link 152, in other embodiments the first and third links 132, 152 can have approximately the same orientation. The links 130 can be configured to couple to each other in a variety of ways, as will be discussed in greater detail below. Further, as illustrated in FIG. 14, disposing the plurality of links 130 in a continued radially offset manner can result in a spiral design that eventually forms an approximately straight line as viewed from a distal end of the elongate member. This configuration can also cause all the plurality of links 130 to pivot in any direction, thereby enabling the plurality of links 30 to achieve any desired shape.

FIG. 15 illustrates one embodiment of a single link, as shown the second link 142, of the plurality of links 130 of the elongate member. The link 142 can include a pair of opposed arms 144 located on a proximal end 142p of the link 142 and a pair of opposed arms 146 located on a distal end 142d of the link 142. The opposed arms 144, 146 can be configured to extend into a receiving portion in respective distal and proximal ends of adjacent links. As illustrated, the opposed arms 144 of the proximal end 142p extend in a plane A' that is substantially perpendicular to a plane B' containing the opposed arms 146 of the distal end 142d. The individuals arms of the opposed arms 144, 146 can have any thickness, including a substantially similar thickness, but in the illustrated embodiment one of the arms of each of the opposed arms 144, 146 is thicker than a second arm of the opposed arms 144, 146. The link 142 can further include one or more receiving portions 148, 150 for receiving opposed arms of adjacent links. In the illustrated embodiment, although only two receiving portions 148, 150 are viewable, two additional receiving portions are included in the walls opposite of the receiving portions 148, 150. While the receiving portions 148, 150 can be configured in a variety of manners, in the illustrated embodiment the receiving portions 148, 150 are substantially A-shaped. More particularly, bases 148b, 150b of the A-shaped receiving portions 148, 150 can include channels 147, 149 in which distal ends of opposed arms of an adjacent link can be received. The substantially A-shaped receiving portions 148, 150 can also include apexes 148a, 150a. The bases 148b, 150b of the receiving portions 148, 150 can each include abutments 151, 153 disposed therein that are configured to prevent movement of arms within the receiving portions 148, 150 when the arms are in the locked position. The abutments 151, 153 can also assist in preventing the arms from sliding past an approximate center portion of the receiving portions 148, 150 to the other side of the receiving portions 148, 150, i.e., the side in which the arms are not disposed when in the locked position. As discussed in greater detail below, in a locked position distal ends of arms in an adjacent link can be located in end 147e, 149e of the channels 147, 149 of the receiving portions 148, 150 while proximal ends of arms of an adjacent link can be spaced apart from the apexes 148a, 150a of the receiving portions 148, 150. The abutments 151, 153 in the bases 148b, 150b of the receiving portions 148, 150 can prevent movement of the arms in the locked position. When the arms are not disposed against the abutments 151, 153 in the bases 148b, 150b of the receiving portion 148, 150, the arms can be in the unlocked position, in which they are free to slide and pivot up to center, tip portions of the abutments 151, 153. When the arm reaches the center, tip portions of the abutments 151, 153, a top of the abutment 151, 153 can prevent the arms from becoming displaced to the other side of the channel 147, 149.

The link 142 can further be divided into a first portion 170 and a second portion 172 with each portion having a first end 170a, 172a and a second end 170b, 172b, respectively. Each of the first and second portions 170, 172 can be configured in substantially the same manner, thereby easing the manufacture and repair of each portion 170, 172 of the link 142, and in the illustrated embodiment the first portion 170 is radially offset from the second portion 172 by about 90 degrees. The second ends 170b, 172b of each of the first and second portions 170, 172 can be coupled together to form the link 142. In the illustrated embodiment the second ends 170b, 172b are fixedly mated to each other, for example by way of an adhesive, welding, mechanical attachment, or other mating techniques. While in the illustrated embodiment the link 142 includes the first and second portions 170, 172, in other embodiments the link 142 can be a unitary structure, can include more than two portions, or can be made of two or more portions that are not substantially similar.

Figure 16A:
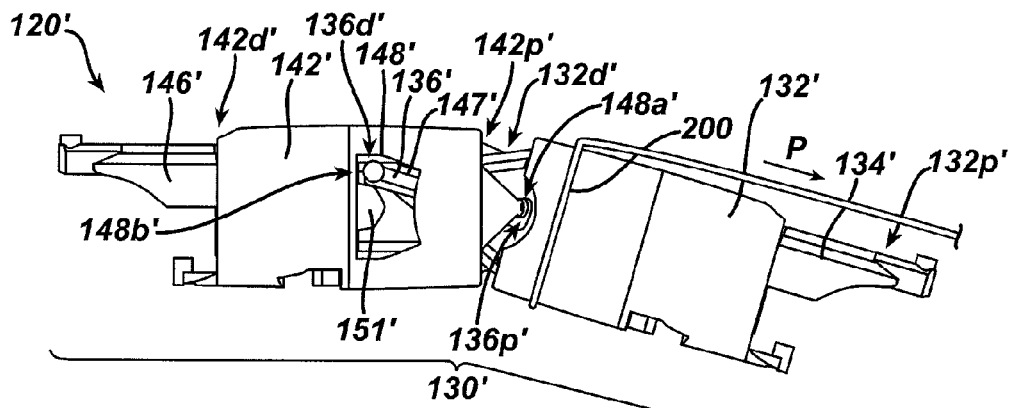
FIG. 16A is a side view of another exemplary embodiment of a stiffening element for an endoscopic surgical device in a first, locked position.
Figure 16B:
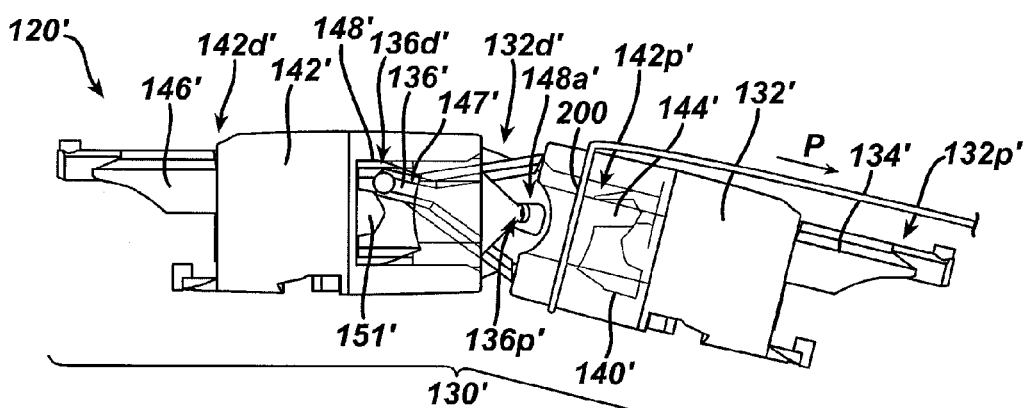
FIG. 16B is a partially transparent side view of the stiffening element of FIG. 16A in a second, intermediate unlocked position.
Figure 16C:
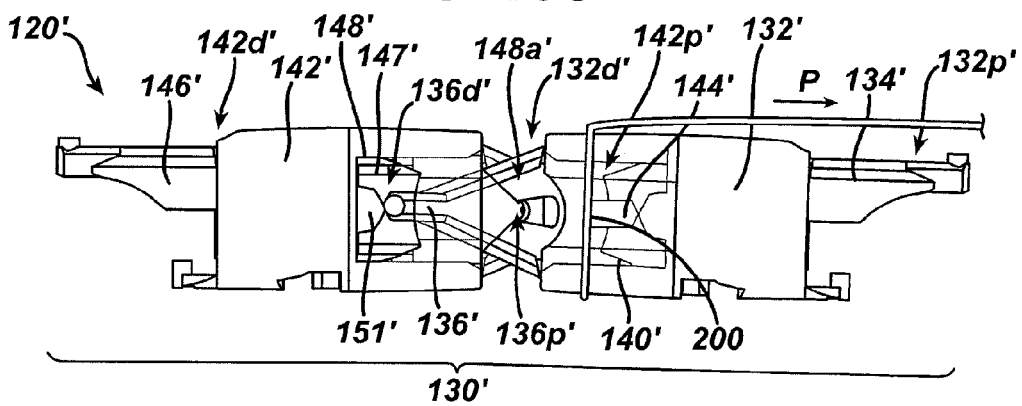
FIG. 16C is a partially transparent side view of the stiffening element of FIG. 16A in a third, unlocked position.

Movement of the links 130 between unlocked and locked positions can be achieved using a variety of different actuating members, but in one embodiment, illustrated in FIGS. 16A-16C, a cable 200 is used to move the plurality of links 130 between the unlocked and locked positions. While in the illustrated embodiment the cable 200 is disposed alongside a stiffening element 120', in other embodiments part or all of the cable 200 can be disposed within the stiffening element 120'. The cable 200 can generally be configured to push and/or pull a plurality of links 130' of the stiffening element 120' together and apart to move it between the unlocked and locked configurations. As discussed above, the links 130' can be axially compressed, so in order to move the links 130' from a locked configuration to an unlocked configuration, the cable 200 can be pulled. When tension on the cable 200 is released, the links 130' can return to the locked configuration to assume a desired configuration. In other embodiments the links can be designed in the opposite manner such that pulling on the cable 200 places the links 130' in the locked configuration while releasing the tension in the cable 200 places the links 130' in the unlocked configuration.

The stiffening element 120' illustrated in FIGS. 16A-16C is used in a similar manner to the stiffening element 120 of FIGS. 13A-15. The stiffening element 120' includes a plurality of links 130' and a first link 132' and a second link 142' of the plurality of links 130'. In this particular embodiment, the pair of opposed arms of the stiffening element 120 are replaced by a single arm 134', 136', 144', 146' in each of the proximal and distal ends 132p', 132d', 142p', 142d' of each link 132', 142', respectively. One arm 136' is configured to be disposed in a receiving portion 148' of the adjacent link 142' while the other arm 134' is configured to be disposed in a receiving portion of another adjacent link (not illustrated). In the illustrated embodiment, the arm 134' of the proximal end 132p' of the first link 132' and the arm 146' of the distal end 142d' of the second link 142' are configured to engage adjacent links which are not illustrated, the arm 136' of the distal end 132d' of the link 132' is disposed in receiving portion 148' of the proximal end 142p' of the second link 142', and the arm 144' of the proximal end 142p' of the link 142' is disposed in the receiving portion 140' of the distal end 132d' of the link 132'.

The links can be slidably and pivotally coupled to one another and operate in a manner similar to that described with respect to the stiffening element of FIGS. 13A-15. As shown in FIG. 16A, the plurality of links 130' are in the locked configuration because a distal end 136d' of the arm 144' is in a base 148b' of the receiving portion 148' and the links 130' are axially compressed. Pulling the cable 200 in a direction P can remove the plurality of links 130' from the locked configuration and move them into the unlocked configuration in which the links 130' can pivot and slide with respect to each other. As shown in FIG. 16B, the links 130' can begin to separate in response to the force provided by the cable 200 and the links 130' can move toward a desired configuration. The links 130' can continue to slide apart, optionally until the links 130' are approximately straight with respect to each other, as shown in FIG. 16C. In FIG. 16C, an abutment 151' can prevent the distal end 136d' of the arm 136' from moving to the other side of a channel 147' of the base 148b' of the receiving portion 148'. While the stiffening element 120' can achieve a substantially straight configuration in the unlocked position as shown in FIG. 16C, a person skilled in the art would recognize that a variety of shapes, including curved configurations, can be achieved in both the unlocked and locked configurations. Further, similar to the stiffening element 20 described with respect to FIGS. 1A-12B, one or more cables, or other actuating members as desired, can be used to provide selective stiffening to one or more portions of the stiffening element 120'.

Figure 17A:
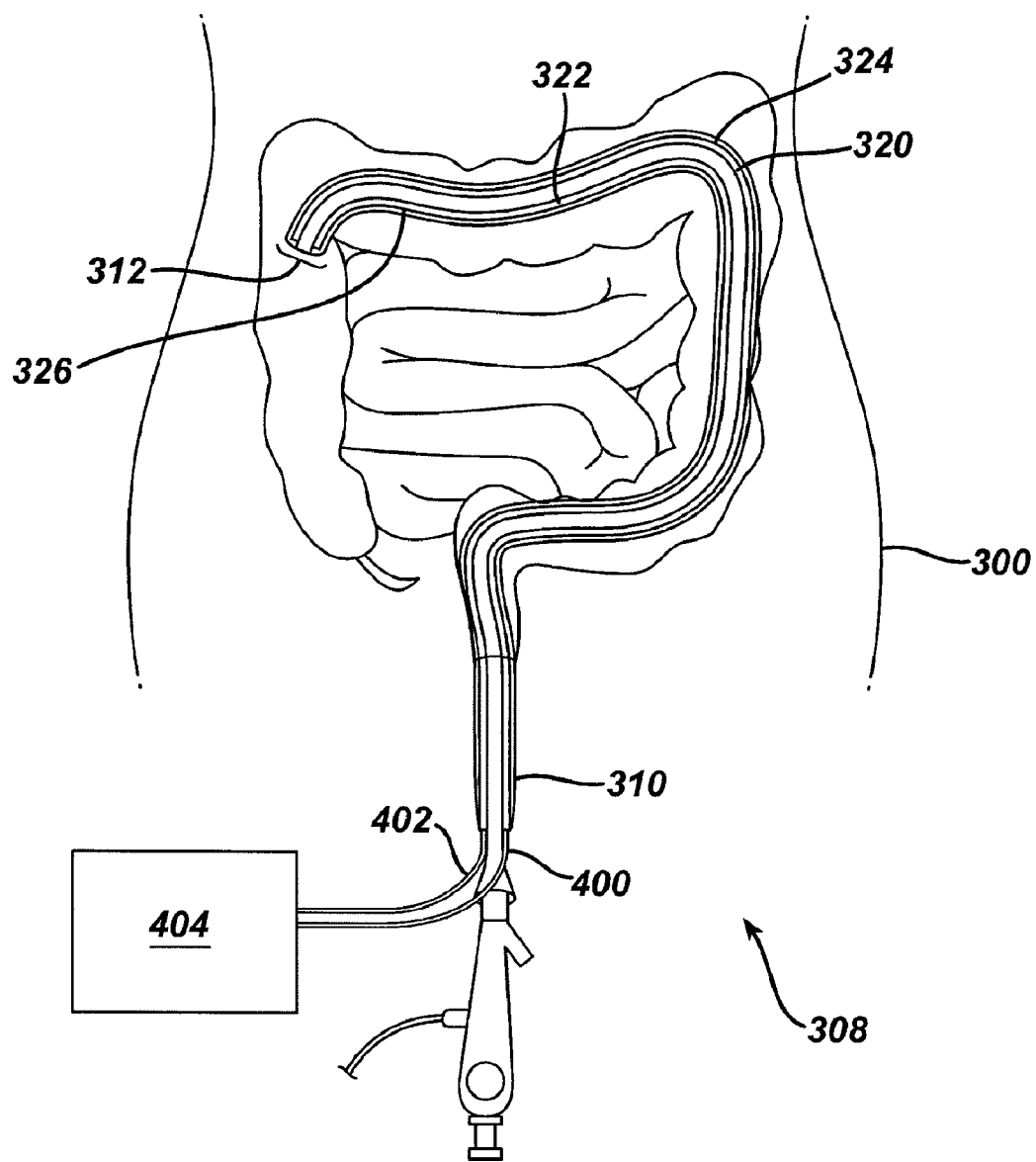
FIG. 17A is a schematic view of one exemplary embodiment of an endoscopic surgical system in use, the system having an endoscope and two stiffening elements.

The stiffening elements described herein can be used as described below to control the placement, positioning, and orientation of an endoscope in a body cavity. Although methods of using such stiffening elements are described with reference to two stiffening elements being used with one endoscope, a person skilled in the art will appreciate that one or more than two stiffening elements per endoscope could alternatively be used. FIG. 17A illustrates one embodiment in which a tool 308 includes an endoscope 310 having a first stiffening element 320 and a second stiffening element 322 disposed within a working channel 312 of the endoscope 310. For purposes of explaining this method, the endoscope 310 includes stiffening elements 320, 322 configured in a manner similar to the stiffening element 20 of FIGS. 1A-12B, and thus the elements 320, 322 can be stiffened by way of expandable members 400, 402, respectively. Expansion and contraction of the expandable members 400, 402 can be achieved by a variety of mechanisms, but as illustrated a two-way pump 404 is used. The stiffening elements 320, 322 can optionally include a sheath 324, 326 disposed around the links of the stiffening elements 320, 322, and thus the links are not visible as shown.

In use, as illustrated in FIG. 17A, the endoscope 310 and the stiffening elements 320, 322 are introduced into the body 300, for example through a natural body orifice (e.g., the anus), and are directed to any number of desired locations. For example, the tool 308 can be advanced through the anus, into the colon, and through a portion of the colon into the peritoneal cavity. The invention is particularly useful to control movement and orientation of the endoscope 310 in relatively larger cavities, such as the peritoneal cavity, that do not constrain all movement of an endoscope.

In general, to navigate through a tortuous path and reach a desired location, the stiffening elements 320, 322 and the endoscope 310 can be progressively and sequentially advanced in a manner that allows the length of the endoscope 310 within the body cavity to increase to reach the desired location. During each stage of the endoscope 310 advancement, its position and/or orientation can be controlled to navigate within the body cavity.

The sequential advancement of the stiffening elements 320, 322 and the endoscope 310 can be achieved using a variety of combinations, but in one exemplary embodiment the endoscope 310 is advanced as follows. First, the endoscope 310 is advanced so as to be distal of the stiffening elements 320, 322 and the portion of the endoscope 310 distal of the stiffening elements 320, 322 can be placed in a desired configuration. Thereafter, the first stiffening element 320 is placed in its unlocked condition and brought to a location adjacent to the distal end of the endoscope 320. Next, the expandable member 400 of the first stiffening element 320 is expanded, thereby stiffening the stiffening element 320 so that it maintains the configuration of the endoscope 310. The endoscope 310 is then advanced to a more distal location. Subsequently, the second stiffening element 322 is placed in the unlocked condition and brought to a location adjacent to the more distal location of the endoscope 310. Next, the expandable member 402 of the second stiffening element 322 is expanded, thereby stiffening the second stiffening element 322 so that it maintains the configuration of the endoscope 310. This sequence of steps is repeated, as necessary, to place the endoscope 310 in the desired position and orientation. At any time that the endoscope 310 is moved distally of all of the stiffening elements 322, 324 it can be configured in a desired orientation, e.g., by turning or bending the distal portion of the endoscope 310 using a mechanism within the endoscope 310. A person skilled in the art will appreciate that prior to moving the first stiffening element 320 from its first location to its second location, the expandable member 400 of the first stiffening element 320 can be at least partially contracted to unlock the links of the first stiffening element 320. Similarly, prior to advancing the second stiffening element 322, its expandable member 402 can be at least partially contracted to unlock the links of the second stiffening element 322. Contraction of the respective expandable members 400, 402 can be done at any point after the endoscope 310 moves distal of the location of the first and second stiffening elements 320, 322.

A person skilled in the art will recognize that the endoscope 310 and one or more of the stiffening elements 320, 322 can be advanced separately or together, and further, that any or all of these components can be retracted separately or together as desired. Likewise, in other embodiments, either or both of the stiffening elements 320, 322 can be advanced to a more distal location prior to advancing the endoscope 310 to a more distal location. Still further, each of the expandable members 400, 402 of the stiffening elements 320, 322 can be expanded or contracted before or after either both of the endoscope 310 and the respective stiffening element 320, 322 is moved.

A person skilled in the art will appreciate that while the method of FIG. 17A is described with reference to stiffening elements 322, 324 disposed within the endoscope 310, the stiffening elements 322, 324 can alternatively be disposed along side the endoscope 310 or along or within mating features of the endoscope 310. Similarly, in lieu of expandable members 400, 402, other locking actuators can be used, such as the cable 200 described with respect to FIGS. 16A-16C. In one exemplary method for controlling a surgical device in a body cavity, a first stiffening element can be advanced into a channel of an endoscopic device that extends into a body cavity. The first stiffening element can be directed to a desired location in the channel and can be enabled to assume a desired configuration that corresponds to a desired configuration of the endoscopic device in the body cavity. Once a desired configuration is achieved, the first stiffening element can be stiffened to allow the first stiffening element to assume the desired configuration. This, in turn, can allow at least a portion of the endoscopic device to be maintained in a desired configuration that corresponds to the desired configuration of the first stiffening element. A second stiffening element can also be advanced into the channel of the endoscopic device, either before, during, or subsequent to the insertion of the first stiffening element into the channel. The second stiffening element can operate in a manner similar to the first stiffening element, or alternatively, it can have a different configuration. The second stiffening element can be directed to a desired location in the channel and can be enabled to assume a desired configuration that corresponds to a desired configuration of the endoscopic device in the body cavity. Once a desired configuration is achieved, the second stiffening element can be stiffened to allow the second stiffening element to assume the desired configuration. This, in turn, can allow at least a portion of the endoscopic device to be maintaining in another desired configuration that corresponds to the desired configuration of the second stiffening element.

As discussed in above with respect to FIG. 17A, and as discussed further below with respect to FIGS. 17B-17F, the first and second stiffening elements can be sequentially moved and locked relative to the endoscopic device to move the endoscopic device relative to the body cavity. By way of non-limiting example, a distal end of the first stiffening element can be positioned adjacent to a distal end of the endoscopic device and subsequently stiffened to allow the first stiffening element, and thus the endoscopic device, to assume corresponding desired configurations. The distal end of the endoscopic device can be advanced distally beyond the distal end of the first stiffening element and then a distal end of the second stiffening element can be positioned adjacent to the distal end of the endoscopic device. The second stiffening element can be stiffened, thereby allowing the second stiffening element, and thus the endoscopic device, to assume corresponding desired configurations. The first stiffening element can be at least partially unstiffened to allow the first stiffening element to be freely movable to assume another desired configuration. Further, the distal end of the endoscopic device can be advanced distally beyond the distal end of the second stiffening element to another desired location. Subsequently, the first stiffening element can be moved adjacent to the distal end of the endoscopic device and the method can be continued as desired. A person skilled in the art will recognize that the portions of the specification related to the various ways of operating one or more stiffening elements in conjunction with an endoscopic device can be used interchangeably, and thus actions such as stiffening and unstiffening the stiffening elements can occur in a variety of ways, at a variety of times, and at a variety of locations, depending on the desired use of the system.

In the embodiment illustrated in FIGS. 17B-17F below, an endoscope 310' of a tool 308' is advanced distally with a first stiffening element 320', the first stiffening element 320' is stiffened, thereby stiffening the endoscope 310', then a second stiffening element 322' is brought to a location proximate to the endoscope 310' and the first stiffening element 320' and is subsequently stiffened. The first stiffening element 320' and the endoscope 310' are then advanced even further distally, the first stiffening element 320' is again stiffened, thereby stiffening the endoscope 310', and then the second stiffening element 322' is unstiffened, brought to a location proximate to the endoscope 310' and the first stiffening element 320', and is subsequently stiffened. The endoscope 310' and each of the two stiffening elements 320', 322', as well components of each device, are configured in a manner similar as described with respect to the endoscope 310 and the two stiffening elements 320, 322. Accordingly, the stiffening elements 320', 322' can optionally include a sheath 324', 326' disposed over the plurality of locks of the stiffening elements 320', 322'. Each of the stiffening elements 320', 322' can also include expandable members 400', 402', which can be expanded and contracted by way of a two-way pump 404'.

Figure 17B:
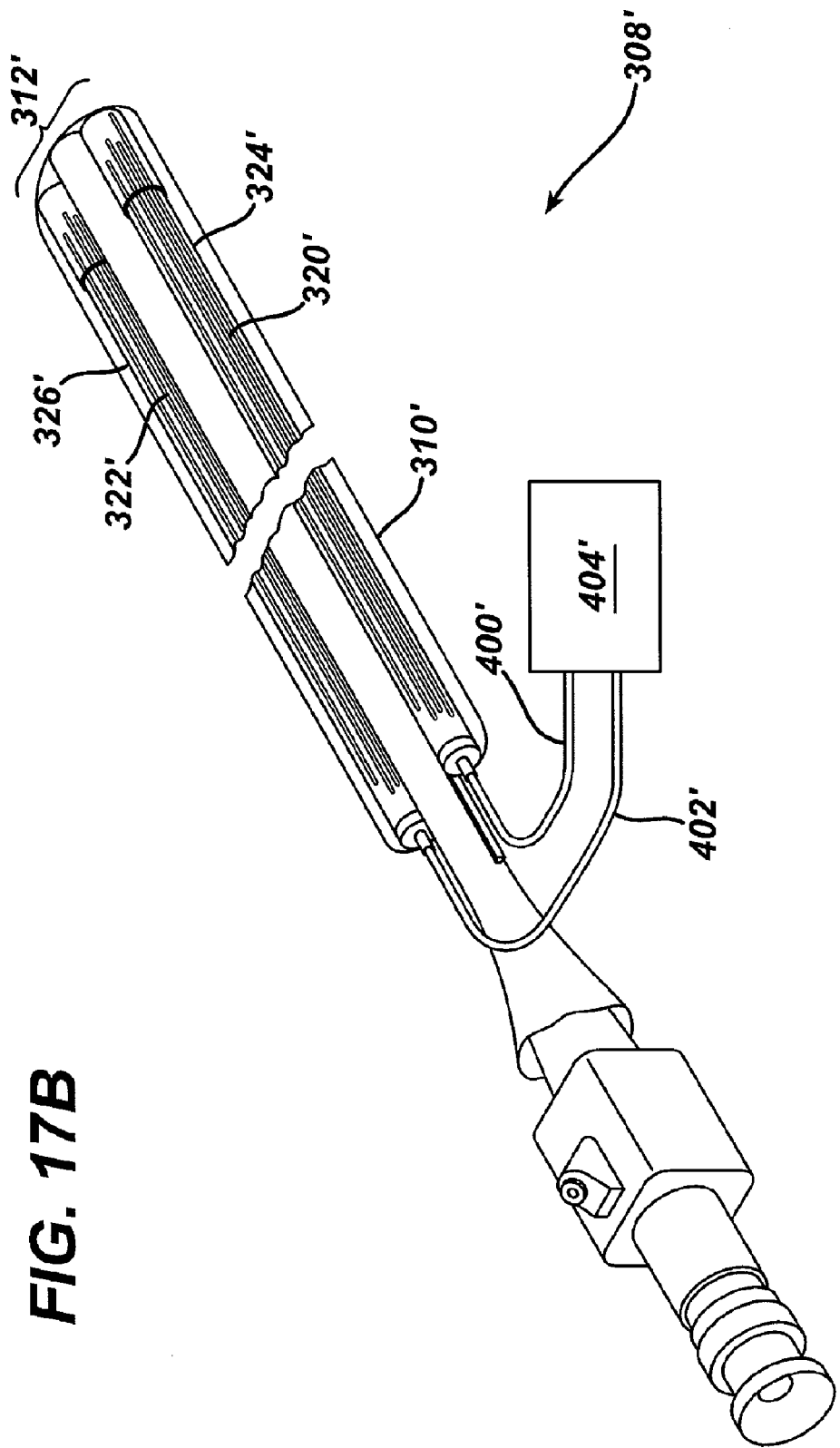
FIGS. 17B-17F are sequential schematic views of another exemplary embodiment of an endoscopic surgical system in use, the system having an endoscope and two stiffening elements.
Figure 17C:
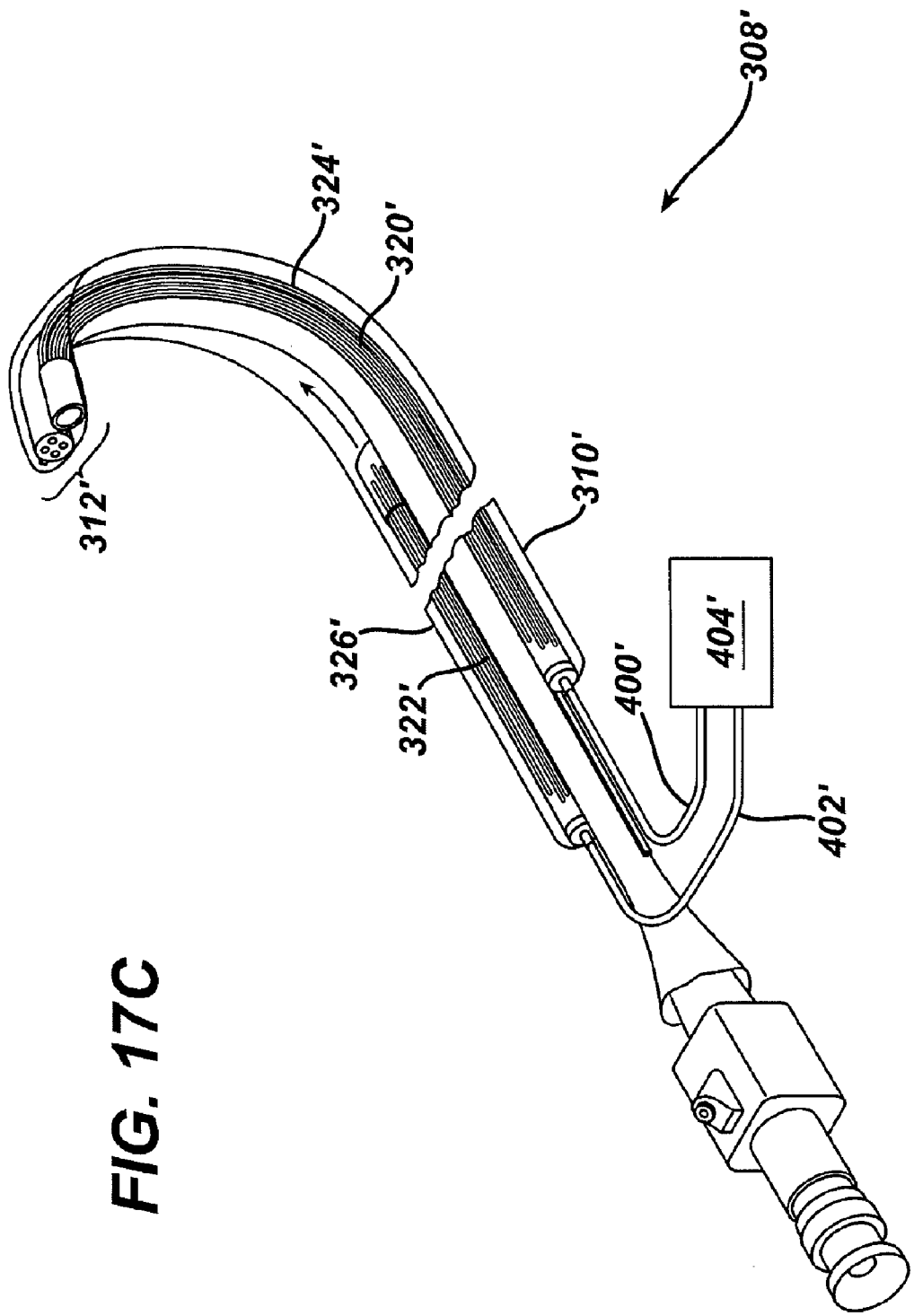
Figure 17D:
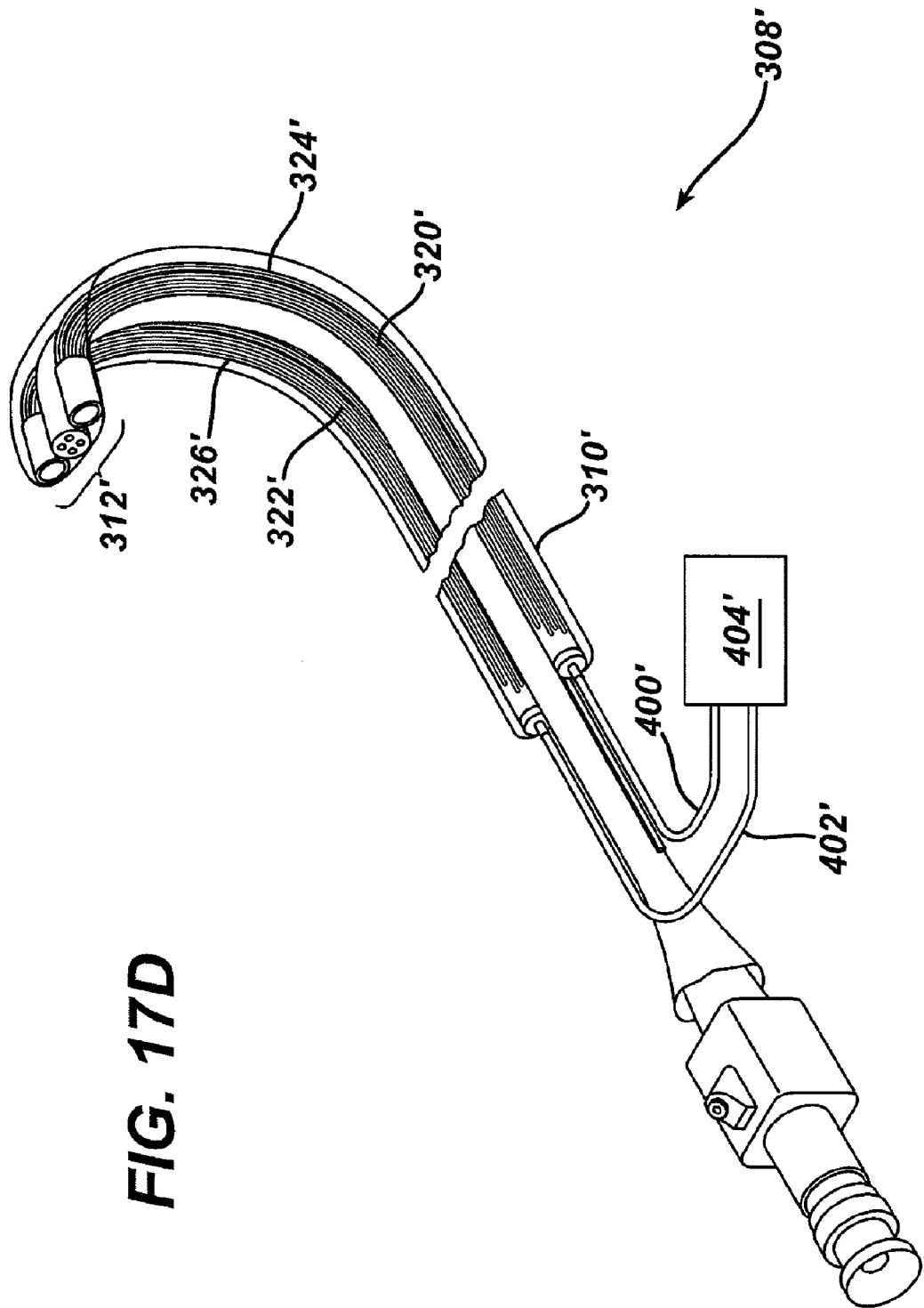

FIG. 17B illustrates the system before either the endoscope 310' or either the first or second stiffening elements 320', 322' is flexed. When the endoscope 310' and the stiffening elements 320', 322' are shown to be at approximately the same position, they can alternatively be disposed distal or proximal with respect to any of the other components. As illustrated in FIG. 17C, the endoscope 310' and the first stiffening element 320' can be moved distally and flexed into a first flexed position. The endoscope 310' and the first stiffening element 320' can be moved concurrently or consecutively in any order. When the endoscope 310' and the first stiffening element 320' have reached a first desired location, in this instance the first flexed position, an expandable member 400' of the first stiffening element 320' can be expanded to place the links of the stiffening element 320' in a locked position conforming to the first flexed position, which in turn can hold the position of the endoscope 310' in the first flexed position. Subsequently, as illustrated in FIG. 17D, either before, during, or after the expandable member 400' of the first stiffening element 320' is expanded to lock the plurality of links, the second stiffening element 322' can be moved distally to approximately the same location as the first stiffening element 320' and the endoscope 310'. An expandable member 402' of the second stiffening element 322' can then be expanded to move its plurality of links into the locked position, thereby conforming to the first flexed position. Alternatively, in another embodiment, the second stiffening element 322' can be moved to a second flexed position that is more distal than the first flexed position and then the expandable member 402' can be expanded. In such an embodiment, the endoscope 310' can also be moved to a second flexed position that is more distal than its first flexed position, which can be proximate to the second flexed position of the second stiffening element 322'. The second stiffening element 322' and the endoscope 310' can move concurrently or consecutively. In one embodiment, the endoscope 310' can move to the second flexed position prior to the second stiffening element 322'.

Figure 17E:
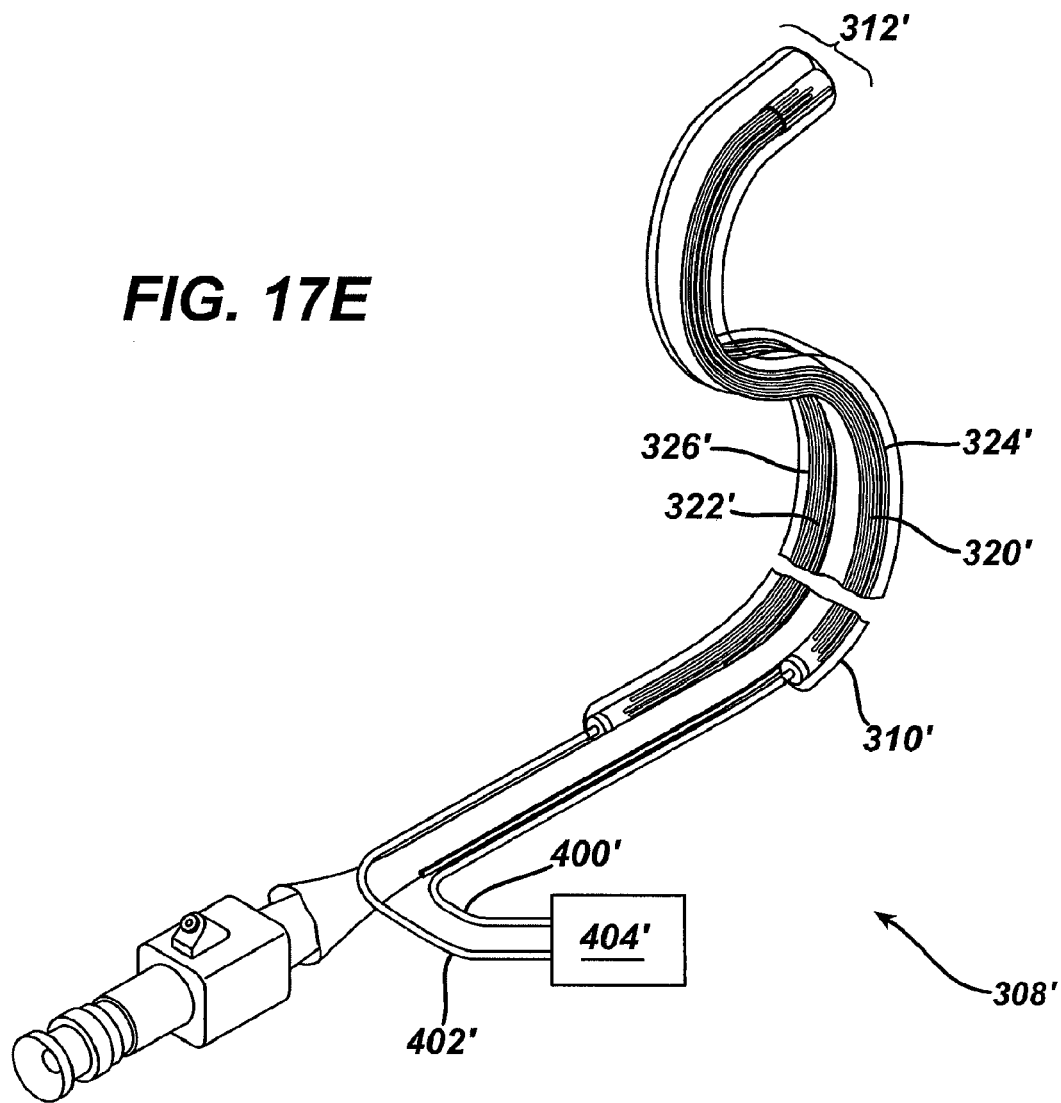
Figure 17F:
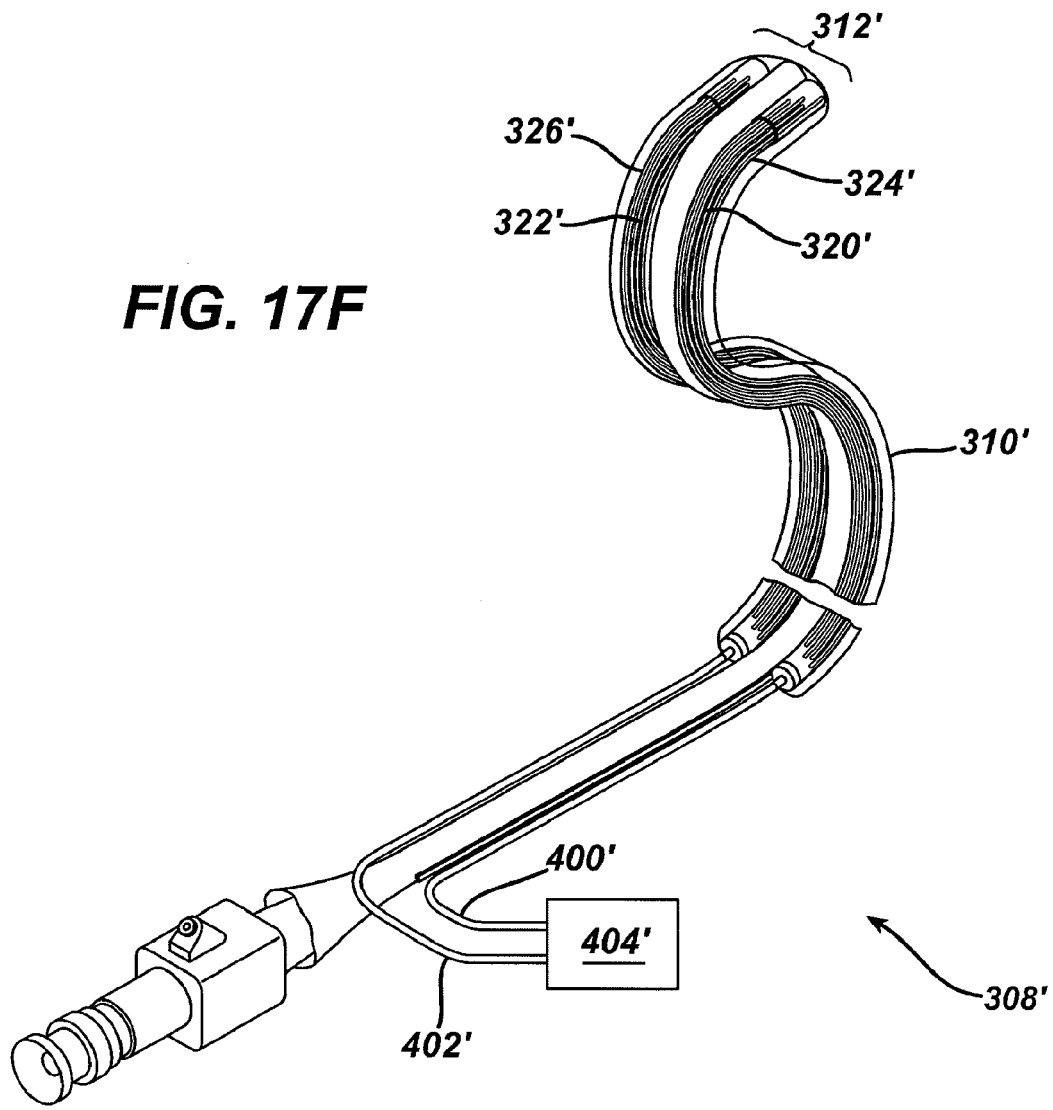

Referring back to the illustrated embodiment, and in particular FIG. 17E in which the second stiffening element 322' is moved proximate to the first flexed position, the expandable member 400' of the first stiffening element 320' can be contracted, the first stiffening element 320' can be advanced distally and flexed into a second flexed position, and the expandable member 400' of the first stiffening element 320' can be expanded again to move its plurality of links into the locked position, thereby conforming to the second flexed position. As illustrated, the endoscope 310' is also advanced distally toward a second flexed position, proximate to the second flexed position of the first stiffening element 320', and is operable in a manner similar to the endoscope 310' in the first flexed position. As such, the endoscope 310' can move concurrently with the first stiffening element 320' to the second flexed position, or alternatively, the two components can move consecutively in either order. Likewise, the second stiffening element 322' can be operable to move and operate in a similar capacity as when the first stiffening element 320' was in the first flexed position. Accordingly, the expandable member 402' of the second stiffening element 322' can be contracted and the second stiffening element 322' can be advanced to a location proximate to the second flexed positions of the endoscope 310' and the first stiffening element 320' and its expandable member 400' can be expanded to provide additional support to the endoscope 310' and the first stiffening element 320' (as illustrated in FIG. 17F), or it can be advanced to a third location, distal to the second flexed position, and operable as previously described. Alternatively, the endoscope 310' can be advanced to a third location, distal to the second flexed position.

In fact, although the order of advancement of the endoscope 310' and the stiffening elements 320', 322' are taught in a few different ways, a person skilled in the art will recognize that these orders are merely examples and that many other combinations of advancement can be used. In some instances it may be desirable to always use the same stiffening element to advance to the next position, while in other instances it may be desirable to alternate in some fashion which stiffening element advances to the next position. Selectively moving and stiffening the endoscope and the stiffening elements allows the device to operate in a "leapfrog" like manner, which is discussed in more particularity in U.S. Patent Publication No. 2008/0200762 of Stokes et al., filed on Feb. 16, 2007, and entitled "Flexible Endoscope Shapelock," which is hereby incorporated by reference in its entirety. Still further, in other embodiments a single stiffening element can be used, and in still other embodiments three or more stiffening elements can be used. One exemplary embodiment of the use of a single stiffening element to advance an endoscope is discussed in U.S. patent application Ser. No. 11/952,475 of Stefanchik et al., filed on Dec. 7, 2007, and entitled "Selective Stiffening Devices and Methods," which was already incorporated by reference in this application in its entirety above.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

A person skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A stiffening element for an endoscopic surgical system, comprising:
 a plurality of links that are pivotally coupled to one another, each link of the plurality of links having a proximal end that includes opposed arms and a distal end that includes opposed arms;
 at least one locking element associated with each link of the plurality of links, the at least one locking element being movable independent from the plurality of links and movable transverse to the longitudinal axis between an unlocked position in which the plurality of links are freely movable to assume a desired configuration, and a locked position in which the locking element engages at least one arm of the opposed arms of the proximal end or the distal end of an adjacent link such that the plurality of links are maintained in a desired configuration; and an actuator extending through the plurality of links and configured to move the at least one locking element between the unlocked and locked positions.

2. The stiffening element of claim 1, wherein the opposed arms of the proximal end of one link of the plurality of links extend in a plane that is substantially perpendicular to a plane containing the opposed arms of the distal end of the one link.

3. The stiffening element of claim 1, wherein the first link is radially offset by about 90° from the second link.

4. The stiffening element of claim 1, wherein the links are configured to compress axially relative to one another when moved from the unlocked position to the locked position.

5. The stiffening element of claim 1, wherein the actuator further comprises an expandable member extending through the plurality of links.

6. The stiffening element of claim 1, wherein the at least one locking element moves in a single plane to move between the unlocked position and the locked position.

7. The stiffening element of claim 1, wherein the diameter of the elongate member is approximately in the range of two to five millimeters.

8. The stiffening element of claim 1, wherein the at least one locking element comprises a first locking element and a second locking element, the first locking element moving in a first plane to move between the unlocked position and the locked position and the second locking element moving in a second plane to move between the unlocked position and the locked position, wherein the first plane is substantially perpendicular to the second plane.

9. A stiffening element for an endoscopic surgical system, comprising:

an elongate member formed from a plurality of links pivotally coupled to one another, each link having a proximal end that includes opposed arms, a distal end that includes opposed arms, and a locking element disposed in the link and slidably movable in a direction transverse to a longitudinal axis of the elongate member between an unlocked position in which links are freely pivotal to allow the elongate member to assume a desired configuration, and a locked position in which the locking element engages at least one arm of the opposed arms of the proximal end or the distal end of an adjacent link such that the links are prevented from pivoting relative to one another to maintain the elongate member in a desired configuration, each locking element moving independent of the link in which it is disposed.

10. The stiffening element of claim 9, wherein the locking element is movable in a direction perpendicular to a longitudinal axis of the elongate member.

11. The stiffening element of claim 9, wherein the locking element comprises first and second locking elements disposed within each link, the first and second locking elements having a substantially identical configuration to each other.

12. The stiffening element of claim 11, wherein the first locking element is disposed within the link at a position that is radially offset from a position of the second locking element in the link.

13. The stiffening element of claim 9, wherein the first link is radially offset by about 90° from the second link.

14. The stiffening element of claim 9, further comprising an expandable member extending through the locking element in each link and configured to move the locking elements between the unlocked and locked positions.

15. The stiffening element of claim 14, wherein the expandable member has a partially expanded position in which the expandable member maintains the locking elements in the unlocked position, and a second fully expanded position in which the expandable member moves the locking elements to the locked position.

16. The stiffening element of claim 14, wherein each locking element has an opening formed therethrough that receives the expandable member therethrough, the opening having an asymmetrical shape.

17. The stiffening element of claim 9, wherein the opposed arms of the proximal end of a link of the plurality of links are received within opposed slots formed on the distal end of an adjacent link, and the opposed arms formed on the distal end of the link of the plurality of links are received within opposed slots formed on the proximal end of an adjacent link, the opposed arms slidably moving within the opposed slots to allow pivotal movement of the links relative to one another.

18. The stiffening element of claim 17, wherein the locking, element has a protrusion that extends into one of the elongate slots to engage the at least one arm of the opposed arms of the proximal end or the distal end of the adjacent link to prevent slidable movement of the arm within the elongate slot when the locking element is in the locked position.

19. The stiffening element of claim 9, wherein the elongate member has a diameter configured for insertion and use in a channel of an endoscope.

20. The stiffening element of claim 19, wherein the diameter of the elongate member is approximately in the range of two to five millimeters.

* * * * *